(12) United States Patent
Schroeder et al.

(10) Patent No.: US 11,859,228 B2
(45) Date of Patent: Jan. 2, 2024

(54) EPIMERASE ENZYMES AND THEIR USE

(71) Applicant: Archer Daniels Midland Company, Decatur, IL (US)

(72) Inventors: William Schroeder, Champaign, IL (US); Padmesh Venkitasubramanian, Forsyth, IL (US); Sridhar Govindarajan, Los Altos, CA (US); Mark Welch, Fremont, CA (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 0 days.

(21) Appl. No.: 17/266,443

(22) PCT Filed: Aug. 7, 2019

(86) PCT No.: PCT/US2019/045400
§ 371 (c)(1),
(2) Date: Feb. 5, 2021

(87) PCT Pub. No.: WO2020/033472
PCT Pub. Date: Feb. 13, 2020

(65) Prior Publication Data
US 2022/0145344 A1    May 12, 2022

Related U.S. Application Data

(60) Provisional application No. 62/716,204, filed on Aug. 8, 2018.

(51) Int. Cl.
*C12P 19/24* (2006.01)
*C12N 9/92* (2006.01)

(52) U.S. Cl.
CPC ............... *C12P 19/24* (2013.01); *C12N 9/92* (2013.01); *C12Y 503/01005* (2013.01)

(58) Field of Classification Search
None
See application file for complete search history.

(56) References Cited

FOREIGN PATENT DOCUMENTS

WO    WO-2016191267 A1 * 12/2016    ............... C12N 9/90

OTHER PUBLICATIONS

Accession B9AYF5. Mar. 24, 2009 (Year: 2009).*
Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*

* cited by examiner

*Primary Examiner* — Christian L Fronda
(74) *Attorney, Agent, or Firm* — Andrew F. Nilles

(57) ABSTRACT

This disclosure provides epimerase enzymes useful for commercial scale production of allulose from fructose. The disclosed enzymes ("epimerase variants") are variants of *Burkholderia multivorans* CGD1 xylose isomerase engineered to have improved catalytic activity of about 1.5- to 2-fold compared with the parent enzyme.

8 Claims, 3 Drawing Sheets

Specification includes a Sequence Listing.

SEQUENCE LISTING

<160> NUMBER OF SEQ ID NOS: 100

<210> SEQ ID NO 1
<211> LENGTH: 5120
<212> TYPE: DNA
<213> ORGANISM: Artificial Sequence
<220> FEATURE:
<223> OTHER INFORMATION: cassette

<400> SEQUENCE: 1

| | | | | | |
|---|---|---|---|---|---|
| taagatgaaa | aacgctgaca | ttgactgggg | acaggtcagt | gaccagctag | ataaagcgaa | 60 |
| agataagatt | acgaaattca | tagaatcaga | tgaaggcaaa | aacttcatcc | agaaagtcat | 120 |
| tgatttcttc | gtatctatct | ggaatgcgat | tgtatctata | ttcaaataag | aaaagcgccg | 180 |
| aaaaatcggc | gtttctttta | ttgctttaca | cccgttttaa | atggcagatc | aagttttaca | 240 |
| atatcttcgt | atgtttctcg | cttcacgact | aaatgagcct | caccgttttc | gacaaataca | 300 |
| acggcgggtc | tcggaatacg | gttataattg | ttggccatgc | tgtatccata | agcgcctgta | 360 |
| caaaaaacgg | caagaagatc | gccttctttt | acttccggca | ggtcaatatc | ccaaatcagc | 420 |
| atatctccgt | tttcacagca | cttccggca | attgataccg | ttttgtcatg | cgcttctccg | 480 |
| atcctgttgg | ctgccgcagc | ttcatattta | gcttggtaaa | gcgcaggacg | aatattgtcg | 540 |
| ttcatgcctc | cgtctacagc | cacatattgg | cggacacccg | gcacttcttt | ttgagagcca | 600 |
| accgtataaa | gagttgtgcc | tgcgtctccc | acgagagaac | ggcccggttc | gatccaaatt | 660 |
| tccggaatgt | caaaaccgta | acgggaagca | ttttctttca | gcatgcttaa | gttattggta | 720 |
| tgactggttt | taagcgcaaa | aaaagttgct | ttttcgtacc | tattaatgta | tcgttttaga | 780 |
| aaaccgactg | taaaaagtac | agtcggcatt | atctcatatt | ataaaagcca | gtcattaggc | 840 |
| ctatctgaca | attcctgaat | agagttcata | acaatcctg | catgataacc | atcacaaaca | 900 |
| gaatgatgta | cctgtaaaga | tagcggtaaa | tatattgaat | tacctttatt | aatgaatttt | 960 |
| cctgctgtaa | taatgggtag | aaggtaatta | ctattattat | tgatatttaa | gttaaaccca | 1020 |
| gtaaatgaag | tccatggaat | aatagaaaga | gaaaaagcat | tttcaggtat | aggtgttttg | 1080 |
| ggaaacaatt | tccccgaacc | attatatttc | tctacatcag | aaaggtataa | atcataaaac | 1140 |
| tctttgaagt | cattctttac | aggagtccaa | ataccagaga | atgttttaga | tacaccatca | 1200 |
| aaaattgtat | aaagtggctc | taacttatcc | caataaccta | actctccgtc | gctattgtaa | 1260 |
| ccagttctaa | aagctgtatt | tgagtttatc | acccttgtca | ctaagaaaat | aaatgcaggg | 1320 |
| taaaatttat | atccttcttg | ttttatgttt | cggtataaaa | cactaatatc | aatttctgtg | 1380 |
| gttatactaa | aagtcgtttg | ttggttcaaa | taatgattaa | atatctcttt | tctcttccaa | 1440 |
| ttgtctaaat | caattttatt | aaagttcatt | tgatatgcct | cctaaatttt | tatctaaagt | 1500 |
| gaatttagga | ggcttacttg | tctgctttct | tcattagaat | caatcctttt | ttaaaagtca | 1560 |
| atattactgt | aacataaata | tatattttaa | aaatatccca | ctttatccaa | ttttcgtttg | 1620 |
| ttgaactaat | gggtgcttta | gttgaagaat | aaagaccaca | ttaaaaaatg | tggtcttttg | 1680 |
| tgttttttta | aaggatttga | gcgtagcgaa | aaatcctttt | cttcttatc | ttgataataa | 1740 |
| gggtaactat | tgccgatcgt | ccattccgac | agcatcgcca | gtcactatgg | cgtgctgcta | 1800 |
| gcgccattcg | ccattcaggc | tgcgcaactg | ttggaaggg | cgatcggtgc | gggcctcttc | 1860 |
| gctattacgc | cagctggcga | aagggggatg | tgctgcaagg | cgattaagtt | gggtaacgcc | 1920 |
| agggttttcc | cagtcacgac | gttgtaaaac | gacggccagt | gaattcgagc | tcaggcctta | 1980 |
| actcacatta | attgcgttgc | gctcactgcc | cgctttccag | tcgggaaacc | tgtcgtgcca | 2040 |

```
gctgcattaa tgaatcggcc aacgcgcggg gagaggcggt ttgcgtattg ggcgccaggg      2100
tggtttttct tttcaccagt gagacgggca acagctgatt gcccttcacc gcctggccct      2160
gagagagttg cagcaagcgg tccacgctgg tttgccccag caggcgaaaa tcctgtttga      2220
tggtggttga cggcgggata taacatgagc tgtcttcggt atcgtcgtat cccactaccg      2280
agatatccgc accaacgcgc agcccggact cggtaatggc gcgcattgcg cccagcgcca      2340
tctgatcgtt ggcaaccagc atcgcagtgg gaacgatgcc ctcattcagc atttgcatgg      2400
tttgttgaaa accggacatg gcactccagt cgccttcccg ttccgctatc ggctgaattt      2460
gattgcgagt gagatattta tgccagccag ccagacgcag acgcgccgag acagaactta      2520
atgggcccgc taacagcgcg atttgctggt gacccaatgc gaccagatgc tccacgccca      2580
gtcgcgtacc gtcttcatgg gagaaaataa tactgttgat gggtgtctgg tcagagacat      2640
caagaaataa cgccggaaca ttagtgcagg cagcttccac agcaatggca tcctggtcat      2700
ccagcggata gttaatgatc agcccactga cgcgttgcgc gagaagattg tgcaccgccg      2760
ctttacaggc ttcgacgccg cttcgttcta ccatcgacac caccacgctg cacccagtt       2820 gatcggcgcg agatttaatc gccgcgacaa tttgcgacgg cgcgtgcagg ccagactgg       2880 aggtggcaac gccaatcagc aacgactgtt tgcccgccag ttgttgtgcc acgcggttgg      2940
gaatgtaatt cagctccgcc atcgccgctt ccacttttc ccgcgttttc gcagaaacgt       3000
ggctggcctg gttcaccacg cgggaaacgg tctgataaga gacaccggca tactctgcga      3060
catcgtataa cgttactggt ttcatcaaaa tcgtctccct ccgtttgaat atttgattga      3120
tcgtaaccag atgaagcact ctttccacta tccctacagt gttatggctt gaacaatcac      3180
gaaacaataa ttggtacgta cgatctttca gccgactcaa acatcaaatc ttacaaatgt      3240
agtctttgaa agtattacat atgtaagatt taaatgcaac cgttttttcg gaaggaaatg      3300
atgacctcgt ttccaccgga attagcttgg taccaaagga ggtaaggatc actagaaaat      3360
tttttaaaaa atctcttgac attggaaggg agatatgtta ttataagaat tgcggaattg      3420
tgagcggata acaattccca tataaaggag gaaggatcca tgaataagtt aggtgtgcac      3480
gcattagttt gggaagcggg ttggagtcgt gatgagtgtg ctcgtgccat cgcacgcacc      3540
gcggaaacgg gatttgactt cattgaagtc ccagcgttag atccggcaag cattgatgca      3600
gagtttactc gcagagagtt agaacgccat gggttgggag taacctttc gcttggactc       3660 gatgcgcaaa cagacattag ttctggtgat ccggaacgcg cagcgcgggg taaagctaaa      3720
ttagacgatg tcttacgtgt agcccgggat tgtggagcga ctcatgtctg tggaattctc      3780
tatagtgcat ttcaaaaaaa tgcagttcct acgacccgtg cgggtgtcgc catggccgcg      3840
gacattttag gacaggtagc tgatactgca gcacaatacg gtattacttt ggggttagaa      3900
gtcgttaacc gttatgagtc aaatgtattg aacaccgcgt cacagggtgt tgaactttgc      3960
gagcgtattg gtcgtcccaa cgtaaaagtg catttagata cgtatcacat gaatattgaa      4020
gagagcgata ttatgagcgc gatcagagat acgggagaca ggctagggta tttccatatt      4080
ggcgattctc atcgtggtta cctgggttcc ggaaacgtcg actttactgc cgtatttagg      4140
gcgctggtat tttctggata tacgggaccg attacatttg agtcattctc cagtagagtc      4200
gtaggacaac cattagaggg aattctggca atttggcgta attatgggg agattcccgc       4260 gatctagcta gtcacgcctt agcatatact cgtgtccagt taaatctgc tcaagaagcc       4320 ctaaaacaag ccgagcgcag tcgcttaccg tgataacccg ggcagcccgc ctaatgagcg      4380
```

```
ggcttttttc acgtcacgcg tccatggaga tctaagcttt cacttttgc ttcagggttt    4440 cagccgtatg gtgatcgagt tcgcctgtta atcgaataca aagcacagat tctttgacat    4500
tcatgtcaat tccaaggctc atgctcattc ctccttgata tgatcggata atgagtgttt    4560
cgatttcgac ggaatgaatt ccttcaccgt gacaaaacta gtggtcattc ggcataatta    4620
cttaaatttt gtccagtctc ccatcgtccg ctttaagaat gtgataaacc cggctttctt    4680
catatcttct tttgcagcaa caggactttc agcgagtact tctccatcct ttttcagaac    4740
aagagtgcca agctcttggc cttttgaat cggagcacta atattgtcct tcatcttgat    4800 ttctttttc acatcgttca tatcctcgcc ttttttcgtc aatattgaaa tcggctcaga    4860
tgtagtgagt tcgataaatt tttgtttccc tttttgacc tttacttttg ctactgtttg    4920
atttcgttta tataaaggat gcgtttcata ttggctaaag gcgaagtcaa gcattttgt    4980 cacttgcgcg tttctttctt taggcgtgct cgctccgaat acaaccgcta tggcccgcat    5040
gtttcctttt ttagccgaag cagtcagaca atatttcgct tcgcctgtat agcctgtttt    5100
tacgccgtct acaccaggat                                                 5120
```

<210> SEQ ID NO 2
<211> LENGTH: 1925
<212> TYPE: DNA
<213> ORGANISM: Artificial Sequence
<220> FEATURE:
<223> OTHER INFORMATION: cassette

<400> SEQUENCE: 2

```
ttattgcttt acaccogttt taaatggcag atcaagtttt acaatatctt cgtatgtttc      60
tcgcttcacg actaaatgag cctcaccgtt ttcgacaaat acaacggcgg gtctcggaat     120
acggttataa ttgttggcca tgctgtatcc ataagcgcct gtacaaaaaa cggcaagaag     180
atcgccttct tttacttccg gcaggtcaat atcccaaatc agcatatctc cgctttcaca     240
gcactttccg gcaattgata ccgttttgtc atgcgcttct ccgatcctgt tggctgccgc     300
agcttcatat ttagcttggt aaagcgcagg acgaatattg tcgttcatgc ctccgtctac     360
agccacatat tggcggacac ccggcacttc ttttttgagag ccaaccgtat aaagagttgt     420
gcctgcgtct cccacgagag aacggcccgg ttcgatccaa atttccggaa tgtcaaaacc     480
gtaacgggaa gcatttctt tcacagcttc gataattttt tcaacgtatt cagtggcatg     540
aagcggttca tcatcttccg tataacgaat gccgaaacct cctccaagat tcagcacctt     600
ggatacaaat gaatatgaat ctctccattc gtctagtttt ttgaagattt tttccgctgc     660
taacacaaaa ccggccgtat caaagatttg cgagccgata tggcaatgga cacccagcag     720
ctgaatgtgt tccgattgta atacttgttc aatggcccgt tcagtttgtc cgttatgaag     780
atcgaaacca aactttgaat cttcctggcc cgttgtaatg tagtcatgcg tatgcgcttc     840
tactccgggc gtgatccgaa gaagaacatc gatggagtga cccgtttctt tacataggtc     900
ttcaagaagc gcgatttcat agaaattatc caccacaatg cagccgatgc ggtgctcaag     960
cgccatccgc agttcttccc tgctcttatt gtttccatga agtggatgc gttctgccgg     1020 aaagcctgct gcaacagccg tatatagctc tcctccggat acgacatcta agaaagtcc     1080 ctcttcctca gcgagctgaa tcattgcgac tgatgagaat gctttgctcg catatgccac     1140
ctgtgctttc agccctgcag aaataaacgc ctgcttaaag cttttagcac gctcacgtat     1200
taaagccaca tcatatacgt aaagaggtgt accatatttc tccgctaaat agagagcatc     1260
cacacctccg atttctaaat gaccatgttg attttgtctg cttgtgccgt gtaagaacaa     1320
```

```
tgtcattccc tctttctccg cttatggatg aaaggacagt tttatggact gtcccttcat    1380
aattaagaca tacattatca tactcttcag tcagtttcaa tgcgatcact gcccgctttc    1440
cagtcgggaa acctgtcgtg ccagctgcat taatgaatcg gccaacgcgc ggggagaggc    1500
ggtttgcgta ttgggcgcca gggtggtttt tcttttcacc agtgagacgg gcaacagctg    1560
attgcccttc accgcctggc cctgagagag ttgcagcaag cggtccacgc tggtttgccc    1620
cagcaggcga aaatcctgtt tgatggtggt tgacggcggg atataacatg agctgtcttc    1680
ggtatcgtcg tatcccacta ccgagatatc cgcaccaacg cgcagcccgg actcggtaat    1740
ggcgcgcatt gcgcccagcg ccatctgatc gttggcaacc agcatcgcag tgggaacgat    1800
gccctcattc agcatttgca tggtttgttg aaaaccggac atggcactcc agtcgccttc    1860
ccgttccgct atcggctgaa tttgattgcg agtgagatat ttatgccagc cagccagacg    1920
cagac                                                                1925
```

```
<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
ttattgcttt acacccgttt taaatgg                                          27

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
tctcactcgc aatcaaattc agccg                                            25

<210> SEQ ID NO 5
<211> LENGTH: 897
<212> TYPE: DNA
<213> ORGANISM: Artificial Sequence
<220> FEATURE:
<223> OTHER INFORMATION: codon optimized sequence for xylose isomerase
      [Burkholderia multivorans CGD1]

<400> SEQUENCE: 5
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaacgcca tgggttggga     180 gtaaccttt cgcttggact cgatgcgcaa acagacatta ttctggtga tccggaacgc      240 gcagcgcggg gtaaagctaa attagacgat gtcttacgtg tagcccggga ttgtggagcg     300
actcatgtct gtggaattct ctatagtgca tttcaaaaaa atgcagttcc tacgacccgt     360
gcgggtgtcg ccatggccgc ggacatttta ggacaggtag ctgatactgc agcacaatac     420
ggtattactt tggggttaga agtcgttaac cgttatgagt caaatgtatt gaacaccgcg     480
tcacagggtg ttgaactttg cgagcgtatt ggtcgtccca acgtaaaagt gcatttagat     540
acgtatcaca tgaatattga agagagcgat attatgagcg cgatcagaga tacgggagac     600
aggctagggt atttccatat tggcgattct catcgtggtt acctgggttc cggaaacgtc     660
```

```
gactttactg ccgtatttag ggcgctggta ttttctggat atacgggacc gattacattt      720
gagtcattct ccagtagagt cgtaggacaa ccattagagg gaattctggc aatttggcgt      780
aatttatggg aagattcccg cgatctagct agtcacgcct tagcatatac tcgtgtccag      840
ttaaaatctg ctcaagaagc cctaaaacaa gccgagcgca gtcgcttacc gtgataa        897
```

<210> SEQ ID NO 6
<211> LENGTH: 297
<212> TYPE: PRT
<213> ORGANISM: Burkholderia multivorans

<400> SEQUENCE: 6

```

<220> FEATURE:
<223> OTHER INFORMATION: coding sequence for variant 230323

<400> SEQUENCE: 7

```
atgaataagt taggtgtgca cgcattagtt tgggaagcgg gttggagtcg tgatgagtgt      60
gctcgtgcca tcgcacgcac cgcggaaacg ggatttgact tcattgaaat tccagcgtta     120
gatccggcaa gcattgatgc agagtttact cgcagagagt tagaacgcca tgggttggga     180
gtaaccttt cgcttggact cgatgcgcaa acagacatta gttctggtga tccggaacgc     240
gcagcggcag gtaaagctaa attagacgat gtcttacgtg tagcccggga ttgtggagcg     300
actcatgtct gtggaattct ctatagtgca tttcaaaaaa atgcagttcc tacgacccgt     360
gcgggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaactttg cgagcgtatt ggtcgtccca cgtaaaagt gcatttagat      540
acgtatcaca tgaatattga agagagcgat attatgagcg cgatcagaga tacgggagac     600
aggctagggt atttccatat tggcgattct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagattcccg cgatctagct agtcacgcct agcatatac tcgtgtccag     840
ttaaaatctg ctcaagaagc cctaaaacaa gccgagcgca gtcgcttacc gtgataa       897
```

<210> SEQ ID NO 8
<211> LENGTH: 297
<212> TYPE: PRT
<213> ORGANISM: Artificial Sequence
<220> FEATURE:
<223> OTHER INFORMATION: variant 230323

<400> SEQUENCE: 8

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Ile Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp His Ala Ala Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
```

```
            180                 185                 190
Ser Ala Ile Arg Asp Thr Gly Asp Arg Leu Gly Tyr Phe His Ile Gly
            195                 200                 205

Asp Ser Asn Arg Gly Tyr Leu Gly Ser Gly Asn Val Asp Phe Thr Ala
        210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295
```

<210> SEQ ID NO 9
<211> LENGTH: 897
<212> TYPE: DNA
<213> ORGANISM: Artificial Sequence
<220> FEATURE:
<223> OTHER INFORMATION: coding sequence for variant 230329

<400> SEQUENCE: 9

```
atgaataagt taggtgtgca cgcattagtt tgggaagcgg gttggagtcg tgatgagtgt      60
gctcgtgcca tcgcacgcac cgcggaaacg ggatttgact tcattgaaat tccagcgtta     120
gatccggcaa gcattgatgc agagtttact cgcagagagt tagaacgcca tgggttggga     180
gtaaccttt cgcttggact cgatgcgcaa acagacatta gttctggtga tccggaacgc     240
gcagcgcggg gtaaagctaa attagacgat gtcttacgtg tagcccggga ttgtggagcg     300
actcatgtct gtggaattct ctatagtgca tttcaaaaaa atgcagttcc tacgacccgt     360
gcgggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgattct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagattcccg cgatctagct agtcacgcct tagcatatac tcgtgtccag     840
ttaaaatctg ctcaagaagc cctaaaacaa gccgagcgca gtcgcttacc gtgataa       897
```

<210> SEQ ID NO 10
<211> LENGTH: 297
<212> TYPE: PRT
<213> ORGANISM: Artificial Sequence
<220> FEATURE:
<223> OTHER INFORMATION: variant 230329

<400> SEQUENCE: 10

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30
```

```
Asp Phe Ile Glu Val Pro Ala Leu Asp Pro Ala Ser Ile Asp Ala Glu
         35                  40                  45

Phe Thr Arg Arg Glu Leu Glu Arg His Gly Leu Gly Val Thr Phe Ser
 50                  55                  60

Leu Gly Leu Asp Ala Gln Thr Asp Ile Ser Ser Gly Asp Pro Glu Arg
 65                  70                  75                  80

Ala Ala Arg Gly Lys Ala Lys Leu Asp Asp Val Leu Arg Val Ala Arg
                 85                  90                  95

Asp Cys Gly Ala Thr His Val Ala Gly Ile Leu Tyr Ser Ala Phe Gln
             100                 105                 110

Lys Asn Ala Val Pro Thr Thr Arg Ala Gly Val Ala Met Ala Ala Asp
         115                 120                 125

Ile Leu Gly Gln Val Ala Asp Thr Ala Ala Gln Tyr Gly Ile Thr Leu
130                 135                 140

Gly Leu Glu Val Val Asn Arg Tyr Glu Ser His Val Leu Asn Thr Ala
145                 150                 155                 160

Ser Gln Gly Val Glu Leu Cys Glu Arg Ile Gly Arg Pro Asn Val Lys
                 165                 170                 175

Val His Leu Asp Thr Tyr His Met Asn Ile Glu Glu Ser Asp Ile Met
             180                 185                 190

Ser Ala Ile Arg Asp Thr Gly Asp Arg Leu Gly Tyr Phe His Ile Gly
         195                 200                 205

Asp Ser His Arg Gly Tyr Leu Gly Ser Gly Asn Val Asp Phe Thr Ala
         210                 215                 220

Val Phe Arg Ala Leu Ala Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                 245                 250                 255

Ala Ile Trp Arg Asn Leu Trp Glu Asp Ser Arg Asp Leu Ala Ser His
             260                 265                 270

Ala Leu Ala Tyr Thr Arg Val Gln Leu Lys Ser Ala Gln Glu Ala Leu
         275                 280                 285

Lys Gln Ala Glu Arg Ser Arg Leu Pro
 290                 295

<210> SEQ ID NO 11
<211> LENGTH: 897
<212> TYPE: DNA
<213> ORGANISM: Artificial Sequence
<220> FEATURE:
<223> OTHER INFORMATION: coding sequence for variant 230333

<400> SEQUENCE: 11
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaacgcca tgggttggga     180 gtaaccttt  cgcttggact cgatgcgcaa acagacatta gttctggtga tccggaacgc     240
gcagcggcag gtaaagctaa attaaaagat gtcttacgtg tagcccggga ttgtggagcg     300
actcatgtct gtggaattct ctatagtgca tttcaaaaaa atgcagttcc tacgacccgt     360
gcgggtgtcg ccatggccgc ggacatttta ggacaggtag ctgatactgc agcacaatac     420
ggtattactt tggggttaga agtcgttaac cgttatgagt caaatgtatt gaacaccgcg     480
tcacagggtg ttgaacttat tgagcgtatt ggtcgtccca acgtaaaagt gcatttagat     540
```

```
acgtatcaca tgaatattga agagagcgat attatgagcg cgatcagaga tacgggagac    600
aggctagggt atttccatat tggcgattct catcgtggtt acctgggttc cggaaacgtc    660
gactttactg ccgtatttag ggcgctggta ttttctggat atacgggacc gattacattt    720
gagtcattct ccagtagagt cgtaggacaa ccattagagg gaattctggc aatttggcgt    780
aatttatggg aagattcccg cgatctagct agtcacgcct tagcatatac tcgtgtccag    840
ttaaaatctg ctcaagaagc cctaaaacaa gccgagcgca gtcgcttacc gtgataa      897
```

```
<210> SEQ ID NO 12
<211> LENGTH: 297
<212> TYPE: PRT
<213> ORGANISM: Artificial Sequence
<220> FEATURE:
<223> OTHER INFORMATION: variant 230333

<400> SEQUENCE: 12

Met Asn Lys Phe Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Leu His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Phe
225                 230                 235                 240

Glu Pro Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295
```

<210> SEQ ID NO 13
<211> LENGTH: 897
<212> TYPE: DNA
<213> ORGANISM: Artificial Sequence
<220> FEATURE:
<223> OTHER INFORMATION: coding sequence for variant 230335

<400> SEQUENCE: 13

```
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaacgcca tgggttggga     180
gtaaccttt cgcttggact cgatgcgcaa acagacatta gttctggtga tccggaacgc      240
gcagcggcag gtaaagctaa attagacgat gtcttacgtg tagcccggga ttgtggagcg     300
actcatgtct gtggaattct ctatagtgca tttcaaaaaa atgcagttcc tacgacccgt     360
gcgggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgattct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagattcccg cgatctagct agtcacgcct agcatatac tcgtgtccag     840
ttaaaatctg ctcaagaagc cctaaaacaa gccgagcgca gtcgcttacc gtgataa      897
```

<210> SEQ ID NO 14
<211> LENGTH: 297
<212> TYPE: PRT
<213> ORGANISM: Artificial Sequence
<220> FEATURE:
<223> OTHER INFORMATION: variant 230335

<400> SEQUENCE: 14

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Val Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Glu Gln Tyr Gly Ile Thr Leu
    130                 135                 140

Gly Leu Glu Val Val Asn Arg Tyr Glu Ser Asn Val Leu Asn Thr Ala
145                 150                 155                 160
```

```
Ser Gln Gly Val Glu Leu Cys Glu Arg Ile Gly Arg Pro Asn Val Lys
            165                 170                 175

Val His Leu Asp Thr Tyr His Met Asn Ile Glu Ser Asp Ile Met
        180                 185                 190

Ser Ala Ile Arg Asp Thr Gly Asp Arg Leu Gly Tyr Phe His Ile Gly
            195                 200                 205

Asp Ser His Arg Gly Tyr Leu Gly Ser Gly Asn Leu Asp Phe Thr Ala
        210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295
```

<210> SEQ ID NO 15
<211> LENGTH: 897
<212> TYPE: DNA
<213> ORGANISM: Artificial Sequence
<220> FEATURE:
<223> OTHER INFORMATION: coding sequence for variant 230338

<400> SEQUENCE: 15

```
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaacgcca tgggttggga     180
gtaacctttt cgcttggact cgatgcgcaa acagacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaaa atgcagttcc tacgacccgt     360
gcgggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgattct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagattcccg cgatctagct agtcacgcct tagcatatac tcgtgtccag     840
ttaaaatctg ctcaagaagc cctaaaacaa gccgagcgca gtcgcttacc gtgataa       897
```

<210> SEQ ID NO 16
<211> LENGTH: 297
<212> TYPE: PRT
<213> ORGANISM: Artificial Sequence
<220> FEATURE:
<223> OTHER INFORMATION: variant 230338

<400> SEQUENCE: 16

Met Asn Lys Leu Gly Val His Ala Leu Val Trp Glu Ala Gly Trp Ser

```
1               5                   10                  15
Arg Asp Glu Cys Ala Arg Ala Ile Ala Arg Thr Ala Glu Thr Gly Phe
                20                  25                  30
Asp Phe Ile Glu Val Pro Ala Leu Asp Pro Ala Ser Ile Asp Ala Glu
                35                  40                  45
Phe Thr Arg Arg Glu Leu Glu Arg His Gly Leu Gly Val Thr Phe Ser
                50                  55                  60
Leu Gly Leu Asp Ala Gln Thr Asp Ile Ser Ser Gly Asp Pro Glu Arg
65                  70                  75                  80
Ala Ala Arg Gly Lys Ala Lys Leu Asp Asp Val Leu Arg Val Ala Arg
                85                  90                  95
Asp Cys Gly Gly Thr His Val Cys Gly Ile Leu Tyr Ser Ala Phe Gln
                100                 105                 110
Lys Asn Ala Val Pro Thr Thr Arg Ala Gly Val Ala Met Ala Ala Asp
                115                 120                 125
Ile Leu Gly Gln Val Ala Asp Thr Ala Ala Gln Tyr Gly Ile Thr Leu
                130                 135                 140
Gly Leu Glu Val Val Asn Arg Tyr Glu Ser Asn Leu Leu Asn Thr Ala
145                 150                 155                 160
Ser Gln Gly Val Glu Leu Cys Glu Arg Ile Gly Arg Pro Asn Val Lys
                165                 170                 175
Val His Leu Asp Thr Tyr His Met Asn Ile Glu Glu Ser Asp Ile Met
                180                 185                 190
Ser Ala Ile Arg Asp Thr Gly Asp Arg Leu Gly Tyr Phe His Ile Gly
                195                 200                 205
Asp Ser His Arg Gly Tyr Leu Gly Ser Gly Asn Val Asp Phe Thr Ala
                210                 215                 220
Ile Phe Arg Ala Leu Val Phe Ser Gly Tyr Thr Gly Pro Ile Thr Phe
225                 230                 235                 240
Glu Ser Phe Ser Ser Arg Val Val Gly Gln Pro Leu Glu Gly Ile Leu
                245                 250                 255
Ala Ile Trp Arg Asn Leu Trp Glu Asp Ser Arg Asp Leu Ala Ser His
                260                 265                 270
Ala Leu Ala Tyr Thr Arg Val Gln Leu Lys Ser Ala Gln Glu Ala Leu
                275                 280                 285
Lys Gln Ala Glu Arg Ser Arg Leu Pro
                290                 295

<210> SEQ ID NO 17
<211> LENGTH: 897
<212> TYPE: DNA
<213> ORGANISM: Artificial Sequence
<220> FEATURE:
<223> OTHER INFORMATION: coding sequence for variant 256407

<400> SEQUENCE: 17
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaacgcca tgggttggga     180 gtaaccttt cgcttggact cgatgcgcaa acagacatta gttctggtga tccggaacgc      240
gcagcgcggg gtaaagctaa attaaaagat gtcttacgtg tagcccggga ttgtggagcg     300
actcatgtct gtggaattct ctatagtgca ctgcaaaaat atgcagttcc tacgaccgca     360
gatggtgtcg ccatggccgc ggacatttta ggacaggtag ctgatactgc agcacaatac     420
```

```
ggtattactt tgggttaga agtcgttaac cgttatgaga caaatgtatt gaacaccgcg    480 tcacaggtg ttgaacttat tgagcgtatt ggtcgtccca acgtaaaagt gcatttagat    540
acgtatcaca tgaatattga agagagcgat attatgagcg cgatcagaga tacgggagac    600
aggctagggt atttccatat tggcgattct catcgtggtt acctgggttc cggaaacgtc    660
gactttactg ccgtatttag ggcgctggta ttttctggat atacgggacc gattacattt    720
gagtcattct ccagtagagt cgtaggacaa ccattagagg gaattctggc aatttggcgt    780
aatttatggg aagattcccg cgatctagct agtcacgcct tagcatatac tcgtgtccag    840
ttaaaatctg ctcaagaagc cctaaaacaa gccgagcgca gtcgcttacc gtgataa      897
```

<210> SEQ ID NO 18
<211> LENGTH: 297
<212> TYPE: PRT
<213> ORGANISM: Artificial Sequence
<220> FEATURE:
<223> OTHER INFORMATION: variant 256407

<400> SEQUENCE: 18

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Lys Asp Val Leu Arg Val Ala Arg
                85                  90                  95

Asp Cys Gly Ala Thr His Val Cys Gly Ile Leu Tyr Ser Ala Leu Gln
            100                 105                 110

Lys Tyr Ala Val Pro Thr Thr Ala Asp Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Thr Asn Val Leu Asn Thr Ala
145                 150                 155                 160

Ser Gln Gly Val Glu Leu Ile Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
```

```
                    275                 280                 285

Lys Gln Ala Glu Arg Ser Arg Leu Pro
        290                 295
```

<210> SEQ ID NO 19
<211> LENGTH: 897
<212> TYPE: DNA
<213> ORGANISM: Artificial Sequence
<220> FEATURE:
<223> OTHER INFORMATION: coding sequence for variant 230339

<400> SEQUENCE: 19

```
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaacgcca tgggttggga     180
gtaaccttt cgcttggact cgatgcgcaa acagacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaaa atgcagttcc tacgacccgt     360
gcgggtgtcg ccatggccgc ggacatttta ggacaggtag ctgatactgc agcacaatac     420
ggtattactt tgggggttaga agtcgttaac cgttatgaga caaatgtatt gaacaccgcg     480
tcacagggtg ttgaactttg cgagcgtatt ggtcgtccca acgtaaaagt gcatttagat     540
acgtatcaca tgaatattga agagagcgat attatgagcg cgatcagaga tacgggagac     600
aggctagggg atttccatat tggcgattct catcgtggtt acctgggttc cggaaacgtc     660
gactttactg ccgtatttag ggcgctggta ttttctggat atacgggacc gattgttttt     720
gagtcattct ccagtagagt cgtaggacaa ccattagagg gaattctggc aatttggcgt     780
aatttatggg aagattcccg cgatctagct agtcacgcct agcatatac tcgtgtccag     840
ttaaaatctg ctcaagaagc cctaaaacaa gccgagcgca gtcgcttacc gtgataa       897
```

<210> SEQ ID NO 20
<211> LENGTH: 297
<212> TYPE: PRT
<213> ORGANISM: Artificial Sequence
<220> FEATURE:
<223> OTHER INFORMATION: variant 230339

<400> SEQUENCE: 20

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Ser Gly Ile Leu Tyr Ser Ala Phe Gln
            100                 105                 110

Lys Asn Ala Val Pro Thr Thr Arg Ala Glu Val Ala Met Ala Ala Asp
        115                 120                 125
```

```
Ile Leu Gly Gln Val Ala Asp Thr Ala Ala Gln Tyr Gly Ile Thr Leu
    130                 135                 140

Gly Leu Glu Val Val Asn Arg Tyr Glu Thr Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
290                 295

<210> SEQ ID NO 21
<211> LENGTH: 897
<212> TYPE: DNA
<213> ORGANISM: Artificial Sequence
<220> FEATURE:
<223> OTHER INFORMATION: coding sequence for variant 248843

<400> SEQUENCE: 21
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaacgcca tgggttggga     180 gtaaccttttt cgcttggact cgatgcgcaa acagacatta gttctggtga tccggaacgc     240
gcagcgcggg gtaaagctaa attaaaagat gtcttacgtg tagcccggga ttgtggagcg     300
actcatgtct gtggaattct ctatagtgca ctgcaaaaaa atgcagttcc tacgacccgt     360
gcgggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgattct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagattccgc agatctagct agtcacgcct tagcatttac tcgtgtccag     840
ttaaaatctg ctcaagaagc cctaaaacaa gccgagcgca gtcgcttacc gtgataa       897

<210> SEQ ID NO 22
<211> LENGTH: 297
<212> TYPE: PRT
<213> ORGANISM: Artificial Sequence
<220> FEATURE:
```

<223> OTHER INFORMATION: variant 248843

<400> SEQUENCE: 22

Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Phe His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Ile Phe Arg Ala Leu Val Phe Ser Gly Tyr Thr Gly Pro Ile Thr Ile
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

<210> SEQ ID NO 23
<211> LENGTH: 897
<212> TYPE: DNA
<213> ORGANISM: Artificial Sequence
<220> FEATURE:
<223> OTHER INFORMATION: coding sequence for variant 248867

<400> SEQUENCE: 23
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaacgcca tgggttggga     180 gtaaccttt cgcttggact cgatgcgcaa acagacatta gttctggtga tccggaacgc     240

```
gcagcgcggg gtaaagctaa attaaaagat gtcttacgtg tagcccggga ttgtggagcg    300
actcatgtct gtggaattct ctatagtgca tttcaaaaat atgcagttcc tacgacccgt    360
gcgggtgtcg ccatggccgc ggacatttta agacaggtag ctgatactgc agcacaatac    420
ggtattactt tggggttaga agtcgttaac cgttatgaga caaatgtatt gaacaccgcg    480
tcacagggtg ttgaacttat tgagcgtatt ggtcgtccca acgtaaaagt gcatttagat    540
acgtatcaca tgaatattga agagagcgat attatgagcg cgatcagaga tacgggatca    600
aggctagggt atttccatat tggcgattct catcgtggtt acctgggttc cggaaacgtc    660
gactttactg ccgtatttag ggcgctggta ttttctggat atacgggacc gattacattt    720
gagtcattct ccagtagagt cgtaggacaa ccattagagg gaattctggc aatttggcgt    780
aatttatggg aagattcccg cgatctagct agtcacgcct agcatatac tcgtgtccag    840 ttaaaatctg ctcaagaagc cctaaaacaa gccgagcgca gtcgcttacc gtgataa       897
```

<210> SEQ ID NO 24
<211> LENGTH: 297
<212> TYPE: PRT
<213> ORGANISM: Artificial Sequence
<220> FEATURE:
<223> OTHER INFORMATION: variant 248867

<400> SEQUENCE: 24

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Glu Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Val
225                 230                 235                 240

Glu Ser Phe Ser Ser Arg Val Val Gly Gln Pro Leu Glu Gly Ile Leu
                245                 250                 255
```

Ala Ile Trp Arg Asn Leu Trp Glu Asp Ser Arg Asp Val Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

<210> SEQ ID NO 25
<211> LENGTH: 897
<212> TYPE: DNA
<213> ORGANISM: Artificial Sequence
<220> FEATURE:
<223> OTHER INFORMATION: coding sequence for variant 248891

<400> SEQUENCE: 25
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaacgcta tgggttggga     180
gtaacctttt cgcttggact cgatgcgcaa acagacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaaa atgcagttcc tacgacccgt     360
gcgggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgaatct catcgtggtt acctgggttc cggaaacgtc     660
gactttactg ccgtatttag ggcgctggta ttttctggat atcaaggacc gattacattt     720
gagtcattct ccagtagagt cgtaggacaa ccattagagg gaattctggc aatttggcgt     780
aatttatggg aagattcccg cgatctagct agtcacgcct agcatatac tcgtgcacag     840 ttaaaatctg ctcaagaagc cctaaaacaa gccgagcgca gtcgcttacc gtgataa       897

<210> SEQ ID NO 26
<211> LENGTH: 297
<212> TYPE: PRT
<213> ORGANISM: Artificial Sequence
<220> FEATURE:
<223> OTHER INFORMATION: variant 248891

<400> SEQUENCE: 26

Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln

|   | 100 |   |   |   | 105 |   |   |   | 110 |   |   |
|---|---|---|---|---|---|---|---|---|---|---|---|
| Lys | Asn | Ala | Val | Pro | Thr | Thr | Arg | Ala | Gly | Val | Ala | Met | Ala | Ala | Asp |
|   |   |   | 115 |   |   |   |   | 120 |   |   |   |   | 125 |

Ala Leu Gly Gln Val Ala Asp Thr Ala Ala Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Asp Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Phe
225                 230                 235                 240

Glu Cys Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

<210> SEQ ID NO 27
<211> LENGTH: 897
<212> TYPE: DNA
<213> ORGANISM: Artificial Sequence
<220> FEATURE:
<223> OTHER INFORMATION: coding sequence for variant 248907

<400> SEQUENCE: 27

| atgaataagt | taggtgtgca | cgcattagtt | tgggaagcgg | gttggagtcg | tgatgagtgt | 60 |
| gctcgtgcca | tcgcacgcac | cgcggaaacg | ggatttgact | tcattgaagt | cccagcgtta | 120 |
| gatccggcaa | gcattgatgc | agagtttact | cgcagagagt | tagaacgcta | tgggttggga | 180 |
| gtaacctttt | cgcttggact | cgatgcgcaa | acagacatta | gttctggtga | tccggaacgc | 240 |
| gcagcgcggg | gtaaagctaa | attaaaagat | gtcttacgtg | tagcccggga | ttgtggagcg | 300 |
| actcatgtct | gtggaattct | ctatagtgca | tttcaaaaaa | atgcagttcc | tacgacccgt | 360 |
| gcgggtgtcg | ccatggccgc | ggacatttta | gacaggtag | ctgatactgc | agcacaatac | 420 |
| ggtattactt | tggggttaga | agtcgttaac | cgttatgaga | caaatgtatt | gaacaccgcg | 480 |
| tcacagggtg | ttgaacttat | tgagcgtatt | ggtcgtccca | acgtaaaagt | gcatttagat | 540 |
| acgtatcaca | tgaatattga | agagagcgat | attatgagcg | cgatcagaga | tacgggagac | 600 |
| aggctagggt | atttccatat | tggcgattct | catcgtggtt | acctgggttc | cggaaacgtc | 660 |
| gactttactg | ccgtatttag | ggcgctggta | ttttctggat | atacgggacc | gattacatttt | 720 |
| gagtcattct | ccagtagagt | cgtaggacaa | ccattagagg | gaattctggc | aatttggcgt | 780 |
| aatttatggg | aagatggccg | cgatctagct | agtcacgcct | agcatatac | tcgtgtccag | 840 |
| ttaaaatctg | ctcaagaagc | cctaaaacaa | gccgagcgca | gtcgcttacc | gtgataa | 897 |

-continued

```
<210> SEQ ID NO 28
<211> LENGTH: 297
<212> TYPE: PRT
<213> ORGANISM: Artificial Sequence
<220> FEATURE:
<223> OTHER INFORMATION: variant 248907

<400> SEQUENCE: 28
```

Met Asn Lys Leu Gly Val His Ala Leu Leu Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Ile Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Arg Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

```
<210> SEQ ID NO 29
<211> LENGTH: 897
<212> TYPE: DNA
<213> ORGANISM: Artificial Sequence
<220> FEATURE:
<223> OTHER INFORMATION: coding sequence for variant 248914

<400> SEQUENCE: 29
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
```

```
gatccggcaa gcattgatgc agagtttact cgcagagagt tagaacgcca tgggttggga      180
gtaacctttt cgcttggact cgatgcgcaa acagacatta gttctggtga tccggaacgc      240
gcagcgcggg gtaaagctaa attaaaagat gtcttacgtg tagcccggga ttgtggagcg      300
actcatgtct gtggaattct ctatagtgca tttcaaaaat atgcagttcc tacgacccgt      360
agaggtgtcg ccatggccgc ggacatttta ggacaggtag ctgatactgc agcacaatac      420
ggtattatgt tggggttaga agtcgttaac cgttatgaga caaatgtatt gaacaccgcg      480
tcacagggtg ttgaacttat tgagcgtatt ggtcgtccca acgtaaaagt gcatttagat      540
acgtatcaca tgaatattga agagagcgat attatgagcg cgatcagaga tacgggagac      600
aggctagggt atttccatat tggcgattct catcgtggtt acctgggttc cggaaacgtc      660
gactttactg ccgtatttag ggcgctggta ttttctggat atacgggacc gattacattt      720
gagtcattct ccagtagagt cgtaggacaa ccattagagg gaattctggc aatttggcgt      780
aatttatggg aagattcccg cgatctagct agtcacgcct tagcatatac tcgtgtccag      840
ttaaaatctg ctcaagaagc cctaaaacaa gccgagcgca gtcgcttacc gtgataa       897
```

<210> SEQ ID NO 30
<211> LENGTH: 297
<212> TYPE: PRT
<213> ORGANISM: Artificial Sequence
<220> FEATURE:
<223> OTHER INFORMATION: variant 248914

<400> SEQUENCE: 30

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Tyr
            20                  25                  30

Asp Phe Ile Glu Leu Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Glu Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220
```

```
Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
            245                 250                 255

Ala Ile Trp Arg Asn Leu Trp Glu Asp Ser Arg Asp Leu Ala Ser His
        260                 265                 270

Ala Leu Ala Tyr Thr Arg Val Gln Leu Lys Ser Ala Gln Glu Ala Leu
    275                 280                 285

Lys Gln Ala Glu Arg Ser Arg Leu Pro
    290                 295
```

<210> SEQ ID NO 31
<211> LENGTH: 897
<212> TYPE: DNA
<213> ORGANISM: Artificial Sequence
<220> FEATURE:
<223> OTHER INFORMATION: coding sequence for variant 248925

<400> SEQUENCE: 31

```
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta    120
gatccggcaa gcattgatgc agattttact cgcagagagt tagaacgcca tgggttggga    180
gtaacctttt cgcttggact cgatgcgcaa acagacatta ttctggtga tccgaacgc     240
gcagcgcggg gtaaagctaa attaaaagat gtcttacgtg tagcccggga ttgtggagcg    300
actcatgtct gtggaattct ctatagtgca tttcaaaaaa atgcagttcc tacgaccgca    360
gcgggtgtcg ccatggccgc ggacatttta ggacaggtag ctgatactgc agcacaatac    420
ggtattactt tggggttaga agtcgttaac cgttatgaga caaatgtatt gaacaccgcg    480
tcacagggtg ttgaacttat tgagcgtatt ggtcgtccca acgtaaaagt gcatttagat    540
acgtatcaca tgaatattga agagagcgat attatgagcg cgatcagaga tacgggatca    600
aggctagggt atttccatat tggcgattct catcgtggtt acctgggttc cggaaacgtc    660
gactttactg ccgtatttag ggcgctggta ttttctggat atacgggacc gattacattt    720
gagtcattct ccagtagagt cgtaggacaa ccattagagg gaattctggc aatttggcgt    780
aatttatggg aagattcccg cgatctagct agtcacgcct tagcatatac tcgtgtccag    840
ttaaaatctg ctcaagaagc cctaaaacaa gccgagcgca gtcgcttacc gtgataa       897
```

<210> SEQ ID NO 32
<211> LENGTH: 297
<212> TYPE: PRT
<213> ORGANISM: Artificial Sequence
<220> FEATURE:
<223> OTHER INFORMATION: variant 248925

<400> SEQUENCE: 32

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80
```

Ala Ala Arg Gly Lys Ala Lys Leu Asp Asp Val Leu Arg Val Ala Arg
            85                  90                  95

Asp Cys Gly Ala Thr His Val Cys Gly Ile Leu Tyr Ser Ala Phe Gln
        100                 105                 110

Lys Asn Ala Val Pro Thr Thr Arg Ala Gly Val Ala Met Ala Ala Asp
            115                 120                 125

Ile Leu Gly Gln Val Ala Asp Thr Ala Glu Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Met
225                 230                 235                 240

Glu Ala Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

<210> SEQ ID NO 33
<211> LENGTH: 897
<212> TYPE: DNA
<213> ORGANISM: Artificial Sequence
<220> FEATURE:
<223> OTHER INFORMATION: coding sequence for variant 256382

<400> SEQUENCE: 33
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaaaaata tggggttgga     180
gtaacctttt cgcttggact cgatgcgcaa acagacatta gttctggtga tccggaacgc     240
gcagcgcggg gtaaagctaa attaaaagat gtcttacgtg tagcccggga ttgtggagcg     300
actcatgtct gtggaattct ctatagtgca ctgcaaaaaa atgcagttcc tacgacccgt     360
agaggtgtcg ccatggccgc ggacatttta gacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgattct catcgtggtt acctgggttc cggaaacgtc     660
gactttactg ccgtatttag ggcgctggta tttctggat atacgggacc gattacattt     720
gagtcattct ccagtagagt cgtaggacaa ccattagagg gaattctggc aatttggcgt     780
aatttatggg aagatggccg cgatctagct agtcacgcct tagcatatac tcgtgtccag    840
ttaaaatctg ctcaagaagc cctaaaacaa gccgagcgca gtcgcttacc gtgataa      897

<210> SEQ ID NO 34
<211> LENGTH: 297
<212> TYPE: PRT
<213> ORGANISM: Artificial Sequence
<220> FEATURE:
<223> OTHER INFORMATION: variant 256382

<400> SEQUENCE: 34

Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Tyr
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp His Ala Ala Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Leu Arg Val Gln Leu Lys Ser Ala Gln Glu Ala Leu
        275                 280                 285

Lys Gln Ala Glu Arg Ser Arg Leu Pro
    290                 295

<210> SEQ ID NO 35
<211> LENGTH: 897
<212> TYPE: DNA
<213> ORGANISM: Artificial Sequence
<220> FEATURE:
<223> OTHER INFORMATION: coding sequence for variant 256406

<400> SEQUENCE: 35

```
atgaataagt taggtgtgca cgcattagtt tgggaagcgg gttggagtcg tgatgagtgt    60
gctcgtgcca tcgcacgcac cgcggaaacg ggatttgact tcattgaagt cccagcgtta   120
gatccggcaa gcattgatgc agagtttact cgcagagagt tagaaaaaca tgggttggga   180
gtaacctttt cgcttggact cgatgcgcaa acagacgtta gttctggtga tccggaacgc   240
gcagcgcggg gtaaagctaa attaaaagat gtcttacgtg tagcccggga ttgtggagcg   300
actcatgtct gtggaattct ctatagtgca tttcaaaaat atgcagttcc tacgacccgt   360
agaggtgtcg ccatggccgc ggacatttta ggacaggtag ctgatactgc agcacaatac   420
ggtattactt tggggttaga agtcgttaac cgttatgaga caaatgtatt gaacaccgcg   480
tcacagggtg ttgaacttat tgagcgtatt ggtcgtccca acgtaaaagt gcatttagat   540
acgtatcaca tgaatattga agagagcgat attatgagcg cgatcagaga tacgggagac   600
aggctagggt atttccatat tggcgattct catcgtggtt acctgggttc cggaaacgtc   660
gactttactg ccgtatttag ggcgctggta ttttctggat atacgggacc gattacattt   720
gagtcattct ccagtagagt cgtaggacaa ccattagagg gaattctggc aatttggcgt   780
aatttatggg aagatggccg cgatctagct agtcacgcct agcatatac tcgtgtccag   840
ttaaaatctg ctcaagaagc cctaaaacaa gccgagcgca gtcgcttacc gtgataa      897
```

<210> SEQ ID NO 36
<211> LENGTH: 297
<212> TYPE: PRT
<213> ORGANISM: Artificial Sequence
<220> FEATURE:
<223> OTHER INFORMATION: variant 256406

<400> SEQUENCE: 36

```
Met Asn Lys Leu Gly Val His Ala Leu Val Trp Glu Ala Gly Trp Ser
  1               5                  10                  15

Arg Asp Glu Cys Ala Arg Ala Ile Ala Arg Thr Ala Glu Thr Gly Phe
             20                  25                  30

Asp Phe Ile Glu Val Pro Ala Leu Asp Pro Ala Ser Ile Asp Ala Glu
         35                  40                  45

Phe Thr Arg Arg Glu Leu Glu Arg His Gly Leu Gly Val Thr Phe Ser
     50                  55                  60

Leu Gly Leu Asp Ala Gln Thr Asp Ile Ser Ser Gly Asp Pro Glu Arg
 65                  70                  75                  80

Ala Ala Arg Gly Lys Ala Lys Leu Lys Asp Val Leu Arg Val Ala Arg
                 85                  90                  95

Asp Cys Gly Ala Thr His Val Cys Gly Pro Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Val His Ile Gly
```

```
                195                 200                 205

Asp Ser Asn Arg Gly Tyr Leu Gly Ser Gly Asn Val Asp Phe Thr Ala
        210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
290                 295

<210> SEQ ID NO 37
<211> LENGTH: 897
<212> TYPE: DNA
<213> ORGANISM: Artificial Sequence
<220> FEATURE:
<223> OTHER INFORMATION: coding sequence for variant 255290

<400> SEQUENCE: 37
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaacgcca tgggttggga     180
gtaacctttt cgcttggact cgatgcgcaa acagacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaat atgcagttcc tacgacccgt     360
agaggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgattct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagattcccg cgatctagct agtcacgcct tagcatatac tcgtgtccag     840
ttaaaatctg ctcaagaagc cctaaaacaa gccgagcgca gtcgcttacc gtgataa       897

<210> SEQ ID NO 38
<211> LENGTH: 297
<212> TYPE: PRT
<213> ORGANISM: Artificial Sequence
<220> FEATURE:
<223> OTHER INFORMATION: variant 255290

<400> SEQUENCE: 38

Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
                20                  25                  30

Asp Phe Ile Glu Val Pro Ala Leu Asp Pro Ala Ser Ile Asp Ala Glu
            35                  40                  45
```

```
Phe Thr Arg Arg Glu Leu Glu Arg His Gly Leu Gly Val Thr Phe Ser
 50                  55                  60
Leu Gly Leu Asp Ala Gln Thr Asp Ile Ser Ser Gly Asp Pro Glu Arg
 65                  70                  75                  80
Ala Ala Arg Gly Lys Ala Lys Leu Asp Asp Val Leu Arg Val Ala Arg
                 85                  90                  95
Asp Cys Gly Ala Thr His Val Cys Gly Ile Leu Tyr Ser Ala Phe Gln
                100                 105                 110
Lys Asn Ala Val Pro Thr Thr Arg Ala Gly Val Ala Met Ala Ala Asp
                115                 120                 125
Ile Leu Gly Gln Val Ala Asp Thr Ala Ala Gln Tyr Gly Ile Thr Leu
130                 135                 140
Gly Leu Glu Val Val Asn Arg Tyr Glu Thr Tyr Val Leu Asn Thr Ala
145                 150                 155                 160
Ser Gln Gly Val Glu Leu Cys Glu Arg Ile Gly Arg Pro Asn Val Lys
                165                 170                 175
Val His Leu Asp Thr Tyr His Met Asn Ile Glu Glu Ser Asp Ile Met
                180                 185                 190
Ser Ala Ile Arg Asp Thr Gly Asp Arg Leu Gly Tyr Phe His Ile Gly
                195                 200                 205
Asp Ser His Arg Gly Tyr Leu Gly Ser Gly Asn Val Asp Phe Thr Ala
                210                 215                 220
Val Phe Arg Ala Leu Val Phe Ser Gly Tyr Thr Gly Pro Ile Thr Leu
225                 230                 235                 240
Glu Ser Phe Ser Ser Arg Val Val Gly Gln Pro Leu Glu Gly Ile Leu
                245                 250                 255
Ala Ile Trp Arg Asn Leu Trp Glu Asp Ser Arg Asp Leu Ala Ser His
                260                 265                 270
Ala Leu Ala Tyr Thr Arg Val Gln Leu Lys Ser Ala Gln Glu Ala Leu
                275                 280                 285
Lys Gln Ala Glu Arg Ser Arg Leu Pro
                290                 295

<210> SEQ ID NO 39
<211> LENGTH: 897
<212> TYPE: DNA
<213> ORGANISM: Artificial Sequence
<220> FEATURE:
<223> OTHER INFORMATION: coding sequence for variant 257999

<400> SEQUENCE: 39
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaaaaaca tgggttggga     180
gtaaccttt cgcttggact cgatgcgcaa acagacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaat atgcagttcc tacgacccgt     360
agaggtgtcg ccatggccgc ggacattta ggacaggtag ctgatactgc agcacaatac     420
ggtattactt tggggttaga agtcgttaac cgttatgaga caatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgattct catcgtggtt acctgggttc cggaaacgtc     660
```

```
gactttactg ccgtatttag ggcgctggta ttttctggat atacgggacc gattacattt    720
gagtcattct ccagtagagt cgtaggacaa ccattagagg gaattctggc aatttggcgt    780
aatttatggg aagatggccg cgatctagct agtcacgcct tagcatatac tcgtgtccag    840
ttaaaatctg ctcaagaagc cctaaaacaa gccgagcgca gtcgcttacc gtgataa      897
```

<210> SEQ ID NO 40
<211> LENGTH: 297
<212> TYPE: PRT
<213> ORGANISM: Artificial Sequence
<220> FEATURE:
<223> OTHER INFORMATION: variant 257999

<400> SEQUENCE: 40

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Gly Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Leu Asp Phe Thr Ala
    210                 215                 220

Val Phe Arg Ala Leu Val Phe Ser Gly Tyr Thr Gly Pro Ile Thr Ile
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295
```

<210> SEQ ID NO 41
<211> LENGTH: 897

<212> TYPE: DNA
<213> ORGANISM: Artificial Sequence
<220> FEATURE:
<223> OTHER INFORMATION: coding sequence for variant 261731

<400> SEQUENCE: 41

| | | | | | |
|---|---|---|---|---|---|
| atgaataagt | taggtgtgca | cgcattagtt | tgggaagcgg | gttggagtcg | tgatgagtgt | 60 |
| gctcgtgcca | tcgcacgcac | cgcggaaacg | ggatttgact | tcattgaagt | cccagcgtta | 120 |
| gatccggcaa | gcattgatgc | agagtttact | cgcagagagt | tagaaaaaca | tgggttggga | 180 |
| gtaaccttt | cgcttggact | cgatgcgcaa | acagacatta | gttctggtga | tccggaacgc | 240 |
| gcagcgcggg | gtaaagctaa | attaaaagat | gtcttacgtg | tagcccggga | ttgtggagcg | 300 |
| actcatgtct | gtggaattct | ctatagtgca | tttcaaaaat | atgcagttcc | tacgaccgca | 360 |
| agaggtgtcg | ccatggccgc | ggacatttta | ggacaggtag | ctgatactgc | agcacaatac | 420 |
| ggtattactt | tggggttaga | agtcgttaac | cgttatgaga | caaatgtatt | gaacaccgcg | 480 |
| tcacagggtg | ttgaacttat | tgagcgtatt | ggtcgtccca | acgtaaaagt | gcatttagat | 540 |
| acgtatcaca | tgaatattga | agagagcgat | attatgagcg | cgatcagaga | tacggcagac | 600 |
| aggctagggt | atttccatat | tggcgaatct | catcgtggtt | acctgggttc | cggaaacgtc | 660 |
| gactttactg | ccgtatttag | ggcgctggta | ttttctggat | atacgggacc | gattacattt | 720 |
| gagtcattct | ccagtagagt | cgtaggacaa | ccattagagg | gaattctggc | aatttggcgt | 780 |
| aatttatggg | aagatggccg | cgatctagct | agtcacgcct | tagcatttac | tcgtgtccag | 840 |
| ttaaaatctg | ctcaagaagc | cctaaaacaa | gccgagcgca | gtcgcttacc | gtgataa | 897 |

<210> SEQ ID NO 42
<211> LENGTH: 297
<212> TYPE: PRT
<213> ORGANISM: Artificial Sequence
<220> FEATURE:
<223> OTHER INFORMATION: variant 261731

<400> SEQUENCE: 42

Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp His Ala Ala Gln Tyr Gly Ile Thr Leu
    130                 135                 140

Gly Leu Glu Pro Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

```
Val His Leu Asp Thr Tyr His Met Asn Ile Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Phe
225                 230                 235                 240

Glu Pro Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295
```

<210> SEQ ID NO 43
<211> LENGTH: 897
<212> TYPE: DNA
<213> ORGANISM: Artificial Sequence
<220> FEATURE:
<223> OTHER INFORMATION: coding sequence for variant 261732

<400> SEQUENCE: 43

```
atgaataagt taggtgtgca cgcattagtt tgggaagcgg gttggagtcg tgatgagtgt     60
gctcgtgcca tcgcacgcac cgcggaaacg ggatttgact tcattgaagt cccagcgtta    120
gatccggcaa gcattgatgc agagtttact cgcagagagt tagaaaaaca tgggttggga    180
gtaacctttt cgcttggact cgatgcgcaa tgcgacatta gttctggtga tccggaacgc    240
gcagcgcggg gtaaagctaa attaaaagat gtcttacgtg tagcccggga ttgtggagcg    300
actcatgtct gtggaattct ctatagtgca tttcaaaaat atgcagttcc tacgaccgca    360
agaggtgtcg ccatggccgc ggacatttta ggacaggtag ctgatactgc agcacaatac    420
ggtattactt tggggttaga agtcgttaac cgttatgaga caaatgtatt gaacaccgcg    480
tcacagggtg ttgaacttat tgagcgtatt ggtcgtccca acgtaaaagt gcatttagat    540
acgtatcaca tgaatattga agagagcgat attatgagcg cgatcagaga tacgggagac    600
aggctagggt atttccatat tggcgaatct catcgtggtt acctgggttc cggaaacgtc    660
gactttactg ccgtatttag ggcgctggta ttttctggat atacgggacc gattacattt    720
gagtcattct ccagtagagt cgtaggacaa ccattagagg gaattctggc aatttggcgt    780
aatttatggg aagatggccg cgatctagct agtcacgcct tagcatttac tcgtgtccag    840
ttaaaatctg ctcaagaagc cctaaaacaa gccgagcgca gtcgcttacc gtgataa       897
```

<210> SEQ ID NO 44
<211> LENGTH: 297
<212> TYPE: PRT
<213> ORGANISM: Artificial Sequence
<220> FEATURE:
<223> OTHER INFORMATION: variant 261732

<400> SEQUENCE: 44

```
Met Asn Lys Leu Gly Val His Ala Leu Leu Trp Glu Ala Gly Trp Ser
1               5                   10                  15

Arg Asp Glu Cys Ala Arg Ala Ile Ala Arg Thr Ala Glu Thr Gly Phe
```

```
                    20                  25                  30
Asp Phe Ile Glu Val Pro Ala Leu Asp Pro Ala Ser Ile Asp Ala Glu
            35                  40                  45

Phe Thr Arg Arg Glu Leu Glu Arg His Gly Leu Gly Val Thr Phe Ser
        50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Pro Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Val His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295
```

<210> SEQ ID NO 45
<211> LENGTH: 897
<212> TYPE: DNA
<213> ORGANISM: Artificial Sequence
<220> FEATURE:
<223> OTHER INFORMATION: coding sequence for variant 261733

<400> SEQUENCE: 45

```
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaaaaaca tgggttggga     180
gtaacctttt cgcttggact cgatgcgcaa tgcgacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaat atgcagttcc tacgaccgca     360
agaggtgtcg ccatggccgc ggacatttta ggacaggtag ctgatactgc agcacaatac     420
ggtattactt tggggttaga agtcgttaac cgttatgaga caaatgtatt gaacaccgcg     480
```

```
tcacagggtg ttgaacttat tgagcgtatt ggtcgtccca acgtaaaagt gcatttagat    540
acgtatcaca tgaatattga agagagcgat attatgagcg cgatcagaga tacggcagac    600
aggctagggt atttccatat tggcgaatct catcgtggtt acctgggttc cggaaacgtc    660
gactttactg ccgtatttag ggcgctggta ttttctggat atacgggacc gattacattt    720
gagtcattct ccagtagagt cgtaggacaa ccattagagg gaattctggc aatttggcgt    780
aatttatggg aagatggccg cgatctagct agtcacgcct tagcatatac tcgtgtccag    840
ttaaaatctg ctcaagaagc cctaaaacaa gccgagcgca gtcgcttacc gtgataa      897
```

<210> SEQ ID NO 46
<211> LENGTH: 297
<212> TYPE: PRT
<213> ORGANISM: Artificial Sequence
<220> FEATURE:
<223> OTHER INFORMATION: variant 261733

<400> SEQUENCE: 46

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ala Leu Gly Gln Val Ala Asp Thr Ala Ala Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Ile Phe Arg Ala Leu Val Phe Ser Gly Tyr Thr Gly Pro Ile Thr Phe
225                 230                 235                 240

Glu Pro Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
```

<210> SEQ ID NO 47
<211> LENGTH: 897
<212> TYPE: DNA
<213> ORGANISM: Artificial Sequence
<220> FEATURE:
<223> OTHER INFORMATION: coding sequence for variant 261734

<400> SEQUENCE: 47

```
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaaaaaca tgggttggga     180
gtaacctttt cgcttggact cgatgcgcaa tgcgacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaat atgcagttcc tacgaccgca     360
agaggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacggcagac     600
aggctagggt atttccatat tggcgattct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagatggccg cgatctagct agtcacgcct tagcatttac tcgtgtccag     840
ttaaaatctg ctcaagaagc cctaaaacaa gccgagcgca gtcgcttacc gtgataa       897
```

<210> SEQ ID NO 48
<211> LENGTH: 297
<212> TYPE: PRT
<213> ORGANISM: Artificial Sequence
<220> FEATURE:
<223> OTHER INFORMATION: variant 261734

<400> SEQUENCE: 48

Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

```
Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
            165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
            195                 200                 205

Asp Ser His Arg Gly Tyr Leu Gly Ser Gly Asn Val Asp Phe Thr Ala
        210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
            275                 280                 285

Lys Gln Ala Glu Arg Ser Arg Leu Pro
    290                 295
```

<210> SEQ ID NO 49
<211> LENGTH: 897
<212> TYPE: DNA
<213> ORGANISM: Artificial Sequence
<220> FEATURE:
<223> OTHER INFORMATION: coding sequence for variant 261735

<400> SEQUENCE: 49

```
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaaaaaca tgggttggga     180
gtaaccttt cgcttggact cgatgcgcaa tgcgacatta gttctggtga tccggaacgc      240
gcagcgcggg gtaaagctaa attaaaagat gtcttacgtg tagcccggga ttgtggagcg     300
actcatgtct gtggaattct ctatagtgca tttcaaaaat atgcagttcc tacgacccgt     360
agaggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacggcagac     600
aggctagggt atttccatat tggcgaatct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagatggccg cgatctagct agtcacgcct tagcatttac tcgtgtccag     840
ttaaaatctg ctcaagaagc cctaaaacaa gccgagcgca gtcgcttacc gtgataa       897
```

<210> SEQ ID NO 50
<211> LENGTH: 297
<212> TYPE: PRT
<213> ORGANISM: Artificial Sequence
<220> FEATURE:
<223> OTHER INFORMATION: variant 261735

<400> SEQUENCE: 50

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
                35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Ser Gly Ile Leu Tyr Ser Ala Phe Gln
                100                 105                 110

Lys Asn Ala Val Pro Thr Thr Arg Ala Gly Val Ala Met Ala Ala Asp
            115                 120                 125

Ile Leu Gly Gln Val Ala Asp Thr Ala Glu Gln Tyr Gly Ile Thr Leu
130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
                195                 200                 205

Asp Ser His Arg Gly Tyr Leu Gly Ser Gly Asn Val Asp Phe Thr Ala
210                 215                 220

Val Phe Arg Ala Leu Val Phe Ser Gly Tyr Thr Gly Pro Ile Thr Leu
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
275                 280                 285

Lys Gln Ala Glu Arg Ser Arg Leu Pro
290                 295
```

<210> SEQ ID NO 51
<211> LENGTH: 897
<212> TYPE: DNA
<213> ORGANISM: Artificial Sequence
<220> FEATURE:
<223> OTHER INFORMATION: coding sequence for variant 261736

<400> SEQUENCE: 51

```
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaaaaaca tgggttggga     180
gtaacctttt cgcttggact cgatgcgcaa acagacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaat atgcagttcc tacgaccgca     360
```

```
agaggtgtcg ccatggccgc ggacatttta ggacaggtag ctgatactgc agcacaatac    420
ggtattactt tggggttaga agtcgttaac cgttatgaga caaatgtatt gaacaccgcg    480
tcacagggtg ttgaacttat tgagcgtatt ggtcgtccca acgtaaaagt gcatttagat    540
acgtatcaca tgaatattga agagagcgat attatgagcg cgatcagaga tacgggagac    600
aggctagggt atttccatat tggcgaatct catcgtggtt acctgggttc cggaaacgtc    660
gactttactg ccgtatttag gcgctggta ttttctggat atacgggacc gattacatttt    720 gagtcattct ccagtagagt cgtaggacaa ccattagagg gaattctggc aatttggcgt    780
aatttatggg aagatggccg cgatctagct agtcacgcct tagcatttac tcgtgtccag    840
ttaaaatctg ctcaagaagc cctaaaacaa gccgagcgca gtcgcttacc gtgataa      897

<210> SEQ ID NO 52
<211> LENGTH: 297
<212> TYPE: PRT
<213> ORGANISM: Artificial Sequence
<220> FEATURE:
<223> OTHER INFORMATION: variant 261736

<400> SEQUENCE: 52

Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Pro Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val Leu Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Ile Asp Phe Thr Ala
    210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270
```

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

<210> SEQ ID NO 53
<211> LENGTH: 897
<212> TYPE: DNA
<213> ORGANISM: Artificial Sequence
<220> FEATURE:
<223> OTHER INFORMATION: coding sequence for variant 261737

<400> SEQUENCE: 53

```
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta    120
gatccggcaa gcattgatgc agagtttact cgcagagagt tagaaaaaca tgggttggga    180
gtaaccttttt cgcttggact cgatgcgcaa acagacatta gttctggtga tccggaacgc   240
gcagcgcggg gtaaagctaa attaaaagat gtcttacgtg tagcccggga ttgtggagcg    300
actcatgtct gtggaattct ctatagtgca tttcaaaaat atgcagttcc tacgaccgca    360
agaggtgtcg ccatggccgc ggacatttta ggacaggtag ctgatactgc agcacaatac    420
ggtattactt tggggttaga agtcgttaac cgttatgaga caaatgtatt gaacaccgcg    480
tcacagggtg ttgaacttat tgagcgtatt ggtcgtccca acgtaaaagt gcatttagat    540
acgtatcaca tgaatattga agagagcgat attatgagcg cgatcagaga tacggcagac    600
aggctagggt atttccatat tggcgaatct catcgtggtt acctgggttc cggaaacgtc    660
gactttactg ccgtatttag ggcgctggta ttttctggat atacgggacc gattacattt    720
gagtcattct ccagtagagt cgtaggacaa ccattagagg gaattctggc aatttggcgt    780
aatttatggg aagatggccg cgatctagct agtcacgcct tagcatatac tcgtgtccag    840
ttaaaatctg ctcaagaagc cctaaaacaa gccgagcgca gtcgcttacc gtgataa      897
```

<210> SEQ ID NO 54
<211> LENGTH: 297
<212> TYPE: PRT
<213> ORGANISM: Artificial Sequence
<220> FEATURE:
<223> OTHER INFORMATION: variant 261737

<400> SEQUENCE: 54

Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Ser Gly Ile Leu Tyr Ser Ala Phe Gln
            100                 105                 110

Lys Asn Ala Val Pro Thr Thr Arg Ala Gly Val Ala Met Ala Ala Asp

```
            115                 120                 125
Ile Leu Gly Gln Val Ala Asp Thr Ala Ala Gln Tyr Gly Ile Thr Leu
    130                 135                 140

Gly Leu Glu Val Val Asn Arg Phe Glu Ser Asn Leu Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295
```

<210> SEQ ID NO 55
<211> LENGTH: 897
<212> TYPE: DNA
<213> ORGANISM: Artificial Sequence
<220> FEATURE:
<223> OTHER INFORMATION: coding sequence for variant 261738

<400> SEQUENCE: 55

```
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaaaaaca tgggttggga     180
gtaacctttt cgcttggact cgatgcgcaa tgcgacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaat atgcagttcc tacgaccgca     360
agaggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgaatct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagatggccg cgatctagct agtcacgcct agcatatac tcgtgtccag     840
ttaaaatctg ctcaagaagc cctaaaacaa gccgagcgca gtcgcttacc gtgataa      897
```

<210> SEQ ID NO 56
<211> LENGTH: 297
<212> TYPE: PRT

<213> ORGANISM: Artificial Sequence
<220> FEATURE:
<223> OTHER INFORMATION: variant 261738

<400> SEQUENCE: 56

```
Met Asn Lys Ile Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Glu Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Pro Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295
```

<210> SEQ ID NO 57
<211> LENGTH: 897
<212> TYPE: DNA
<213> ORGANISM: Artificial Sequence
<220> FEATURE:
<223> OTHER INFORMATION: coding sequence for variant 261739

<400> SEQUENCE: 57

```
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaaaaaca tgggttggga     180
```

```
gtaaccttt   cgcttggact   cgatgcgcaa   acagacatta   gttctggtga   tccggaacgc   240
gcagcgcggg   gtaaagctaa   attaaaagat   gtcttacgtg   tagcccggga   ttgtggagcg   300
actcatgtct   gtggaattct   ctatagtgca   tttcaaaaat   atgcagttcc   tacgacccgt   360
agaggtgtcg   ccatggccgc   ggacatttta   ggacaggtag   ctgatactgc   agcacaatac   420
ggtattactt   tggggttaga   agtcgttaac   cgttatgaga   caaatgtatt   gaacaccgcg   480
tcacagggtg   ttgaacttat   tgagcgtatt   ggtcgtccca   acgtaaaagt   gcatttagat   540
acgtatcaca   tgaatattga   agagagcgat   attatgagcg   cgatcagaga   tacggcagac   600
aggctagggt   atttccatat   tggcgaatct   catcgtggtt   acctgggttc   cggaaacgtc   660
gactttactg   ccgtatttag   ggcgctggta   ttttctggat   atacgggacc   gattacattt   720
gagtcattct   ccagtagagt   cgtaggacaa   ccattagagg   gaattctggc   aatttggcgt   780
aatttatggg   aagatggccg   cgatctagct   agtcacgcct   tagcatttac   tcgtgtccag   840
ttaaaatctg   ctcaagaagc   cctaaaacaa   gccgagcgca   gtcgcttacc   gtgataa      897
```

<210> SEQ ID NO 58
<211> LENGTH: 297
<212> TYPE: PRT
<213> ORGANISM: Artificial Sequence
<220> FEATURE:
<223> OTHER INFORMATION: variant 261739

<400> SEQUENCE: 58

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Gly Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Asp Gly Val Glu Leu Cys Glu Arg Ile Gly Arg Pro Asn Val Lys
                165                 170                 175

Val Leu Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Phe
225                 230                 235                 240
```

```
Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
290                 295

<210> SEQ ID NO 59
<211> LENGTH: 897
<212> TYPE: DNA
<213> ORGANISM: Artificial Sequence
<220> FEATURE:
<223> OTHER INFORMATION: coding sequence for variant 261740

<400> SEQUENCE: 59
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaaaaaca tgggttggga     180 gtaaccttt  cgcttggact cgatgcgcaa tgcgacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaat atgcagttcc tacgacccgt     360
agaggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgaatct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagatggccg cgatctagct agtcacgcct agcatttac  tcgtgtccag     840 ttaaaatctg ctcaagaagc cctaaaacaa gccgagcgca gtcgcttacc gtgataa       897

<210> SEQ ID NO 60
<211> LENGTH: 297
<212> TYPE: PRT
<213> ORGANISM: Artificial Sequence
<220> FEATURE:
<223> OTHER INFORMATION: variant 261740

<400> SEQUENCE: 60

Met Asn Lys Leu Gly Val His Ala Leu Val Trp Glu Ala Gly Trp Ser
1               5                  10                  15

Arg Asp Glu Cys Ala Arg Ala Ile Ala Arg Thr Ala Glu Thr Gly Phe
            20                  25                  30

Asp Phe Ile Glu Ile Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95
```

```
Asp Cys Gly Ala Thr His Val Ser Gly Ile Leu Tyr Ser Ala Phe Gln
                100                 105                 110

Lys Asn Ala Val Pro Thr Thr Arg Ala Gly Val Ala Met Ala Ala Asp
            115                 120                 125

Ile Leu Gly Gln Val Ala Asp Thr Ala Ala Gln Tyr Gly Ile Thr Leu
        130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Leu Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

<210> SEQ ID NO 61
<211> LENGTH: 897
<212> TYPE: DNA
<213> ORGANISM: Artificial Sequence
<220> FEATURE:
<223> OTHER INFORMATION: coding sequence for variant 261741

<400> SEQUENCE: 61
atgaataagt taggtgtgca cgcattagtt tgggaagcgg gttggagtcg tgatgagtgt     60
gctcgtgcca tcgcacgcac cgcggaaacg ggatttgact tcattgaagt cccagcgtta    120
gatccggcaa gcattgatgc agagtttact cgcagagagt tagaaaaaca tgggttggga    180 gtaaccttt  cgcttggact cgatgcgcaa tgcgacatta gtctggtga tccggaacgc     240 gcagcgcggg gtaaagctaa attaaaagat gtcttacgtg tagcccggga ttgtggagcg    300
actcatgtct gtggaattct ctatagtgca tttcaaaaat atgcagttcc tacgacccgt    360
agaggtgtcg ccatggccgc ggacatttta ggacaggtag ctgatactgc agcacaatac    420
ggtattactt tggggttaga agtcgttaac cgttatgaga caaatgtatt gaacaccgcg    480
tcacagggtg ttgaacttat tgagcgtatt ggtcgtccca acgtaaaagt gcatttagat    540
acgtatcaca tgaatattga agagagcgat attatgagcg cgatcagaga tacggcagac    600
aggctagggt atttccatat tggcgattct catcgtggtt acctgggttc cggaaacgtc    660
gactttactg ccgtatttag ggcgctggta ttttctggat atacgggacc gattacattt    720
gagtcattct ccagtagagt cgtaggacaa ccattagagg gaattctggc aatttggcgt    780
aatttatggg aagatggccg cgatctagct agtcacgcct agcatttac  tcgtgtccag    840 ttaaaatctg ctcaagaagc cctaaaacaa gccgagcgca gtcgcttacc gtgataa       897
```

<210> SEQ ID NO 62
<211> LENGTH: 297
<212> TYPE: PRT
<213> ORGANISM: Artificial Sequence
<220> FEATURE:
<223> OTHER INFORMATION: variant 261741

<400> SEQUENCE: 62

```
Met Asn Lys Phe Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Phe His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Arg Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295
```

<210> SEQ ID NO 63
<211> LENGTH: 897
<212> TYPE: DNA
<213> ORGANISM: Artificial Sequence
<220> FEATURE:
<223> OTHER INFORMATION: coding sequence for variant 261742

<400> SEQUENCE: 63
atgaataagt taggtgtgca cgcattagtt tgggaagcgg gttggagtcg tgatgagtgt    60

```
gctcgtgcca tcgcacgcac cgcggaaacg ggatttgact tcattgaagt cccagcgtta    120
gatccggcaa gcattgatgc agagtttact cgcagagagt tagaaaaaca tgggttggga    180 gtaaccttt  cgcttggact cgatgcgcaa acagacatta gttctggtga tccggaacgc    240
gcagcgcggg gtaaagctaa attaaaagat gtcttacgtg tagcccggga ttgtggagcg    300
actcatgtct gtggaattct ctatagtgca tttcaaaaat atgcagttcc tacgaccgca    360
agaggtgtcg ccatggccgc ggacatttta ggacaggtag ctgatactgc agcacaatac    420
ggtattactt tggggttaga agtcgttaac cgttatgaga caaatgtatt gaacaccgcg    480
tcacagggtg ttgaacttat tgagcgtatt ggtcgtccca acgtaaaagt gcatttagat    540
acgtatcaca tgaatattga agagagcgat attatgagcg cgatcagaga tacggcagac    600
aggctagggt atttccatat tggcgattct catcgtggtt acctgggttc cggaaacgtc    660
gactttactg ccgtatttag ggcgctggta ttttctggat atacgggacc gattacattt    720
gagtcattct ccagtagagt cgtaggacaa ccattagagg gaattctggc aatttggcgt    780
aatttatggg aagatggccg cgatctagct agtcacgcct tagcatttac tcgtgtccag    840
ttaaaatctg ctcaagaagc cctaaaacaa gccgagcgca gtcgcttacc gtgataa     897
```

<210> SEQ ID NO 64
<211> LENGTH: 297
<212> TYPE: PRT
<213> ORGANISM: Artificial Sequence
<220> FEATURE:
<223> OTHER INFORMATION: variant 261742

<400> SEQUENCE: 64

```
Met Asn Lys Leu Gly Val His Ala Leu Val Trp Glu Ala Gly Trp Ser
1               5                  10                  15

Arg Asp Glu Cys Ala Arg Ala Ile Ala Arg Thr Ala Glu Thr Gly Phe
            20                  25                  30

Asp Phe Ile Glu Leu Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Gly Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Ala Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
```

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
            245                 250                 255

Ala Ile Trp Arg Asn Leu Trp Glu Asp Ser Arg Asp Leu Ala Ser His
        260                 265                 270

Ala Leu Ala Tyr Thr Arg Val Gln Leu Lys Ser Ala Gln Glu Ala Leu
    275                 280                 285

Lys Gln Ala Glu Arg Ser Arg Leu Pro
290                 295

<210> SEQ ID NO 65
<211> LENGTH: 897
<212> TYPE: DNA
<213> ORGANISM: Artificial Sequence
<220> FEATURE:
<223> OTHER INFORMATION: coding sequence for variant 261743

<400> SEQUENCE: 65
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaaaaaca tgggttggga     180
gtaacctttt cgcttggact cgatgcgcaa tgcgacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaat atgcagttcc tacgaccgca     360
agaggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgattct catcgtggtt acctgggttc cggaaacgtc     660
gactttactg ccgtatttag ggcgctggta tttttctgga tacgggacc gattacattt     720
gagtcattct ccagtagagt cgtaggacaa ccattagagg gaattctggc aatttggcgt     780
aatttatggg aagatggccg cgatctagct agtcacgcct agcatttac tcgtgtccag     840
ttaaaatctg ctcaagaagc cctaaaacaa gccgagcgca gtcgcttacc gtgataa       897

<210> SEQ ID NO 66
<211> LENGTH: 297
<212> TYPE: PRT
<213> ORGANISM: Artificial Sequence
<220> FEATURE:
<223> OTHER INFORMATION: variant 261743

<400> SEQUENCE: 66

Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

```
Leu Gly Leu Asp Ala Gln Thr Asp Ile Ser Ser Pro Asp Pro Glu Arg
 65                  70                  75                  80

Ala Ala Arg Gly Lys Ala Lys Leu Asp Asp Val Leu Arg Val Ala Arg
                 85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Ile Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Trp Thr Ala
    210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

<210> SEQ ID NO 67
<211> LENGTH: 897
<212> TYPE: DNA
<213> ORGANISM: Artificial Sequence
<220> FEATURE:
<223> OTHER INFORMATION: coding sequence for variant 261744

<400> SEQUENCE: 67
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaaaaaca tgggttggga     180 gtaaccttt  cgcttggact cgatgcgcaa tgcgacatta ttctggtga tccggaacgc      240 gcagcgcggg gtaaagctaa attaaaagat gtcttacgtg tagcccggga ttgtggagcg     300
actcatgtct gtggaattct ctatagtgca tttcaaaaat atgcagttcc tacgacccgt     360
agaggtgtcg ccatggccgc ggacatttta ggacaggtag ctgatactgc agcacaatac     420
ggtattactt tggggttaga agtcgttaac cgttatgaga caatgtatt  gaacaccgcg     480 tcacagggtg ttgaacttat tgagcgtatt ggtcgtccca acgtaaaagt gcatttagat     540
acgtatcaca tgaatattga agagagcgat attatgagcg cgatcagaga tacggcagac     600
aggctagggt atttccatat tggcgaatct catcgtggtt acctgggttc cggaaacgtc     660
gactttactg ccgtatttag ggcgctggta ttttctggat atacgggacc gattacattt     720
```

```
gagtcattct ccagtagagt cgtaggacaa ccattagagg gaattctggc aatttggcgt    780
aatttatggg aagatggccg cgatctagct agtcacgcct tagcatatac tcgtgtccag    840
ttaaaatctg ctcaagaagc cctaaaacaa gccgagcgca gtcgcttacc gtgataa      897
```

<210> SEQ ID NO 68
<211> LENGTH: 297
<212> TYPE: PRT
<213> ORGANISM: Artificial Sequence
<220> FEATURE:
<223> OTHER INFORMATION: variant 261744

<400> SEQUENCE: 68

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Pro Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Leu Asn Arg Tyr Glu Ser Asn Val Leu Asn Thr Ala
145                 150                 155                 160

Ser Glu Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295
```

<210> SEQ ID NO 69
<211> LENGTH: 897
<212> TYPE: DNA
<213> ORGANISM: Artificial Sequence
<220> FEATURE:

<223> OTHER INFORMATION: coding sequence for variant 261745

<400> SEQUENCE: 69

```
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaaaaaca tgggttggga     180
gtaaccttt tcgcttggact cgatgcgcaa tgcgacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaat atgcagttcc tacgaccgca     360
agaggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacggcagac     600
aggctagggt atttccatat tggcgattct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagatggccg cgatctagct agtcacgcct agcatatac tcgtgtccag     840
ttaaaatctg ctcaagaagc cctaaaacaa gccgagcgca gtcgcttacc gtgataa       897
```

<210> SEQ ID NO 70
<211> LENGTH: 297
<212> TYPE: PRT
<213> ORGANISM: Artificial Sequence
<220> FEATURE:
<223> OTHER INFORMATION: variant 261745

<400> SEQUENCE: 70

```
Met Asn Lys Leu Gly Val His Ala Leu Val Trp Glu Ala Gly Trp Ser
  1               5                  10                  15

Arg Asp Glu Cys Ala Arg Ala Ile Ala Arg Thr Ala Glu Thr Gly Phe
             20                  25                  30

Asp Phe Ile Glu Val Pro Ala Leu Asp Pro Ala Ser Ile Asp Ala Glu
         35                  40                  45

Phe Thr Arg Arg Glu Leu Glu Arg His Gly Leu Gly Val Thr Phe Ser
     50                  55                  60

Leu Gly Leu Asp Ala Gln Thr Asp Ile Ser Ser Gly Asp Pro Glu Arg
 65                  70                  75                  80

Ala Ala Arg Gly Lys Ala Lys Leu Asp Asp Val Leu Arg Val Ala Arg
                 85                  90                  95

Asp Cys Gly Ala Thr His Val Cys Gly Pro Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Ser His Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190
```

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Trp Thr Ala
    210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

<210> SEQ ID NO 71
<211> LENGTH: 897
<212> TYPE: DNA
<213> ORGANISM: Artificial Sequence
<220> FEATURE:
<223> OTHER INFORMATION: coding sequence for variant 261746

<400> SEQUENCE: 71
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agattttact cgcagagagt tagaaaaata tgggttggga     180 gtaaccttt cgcttggact cgatgcgcaa acagacatta gttctggtga tccggaacgc      240
gcagcgcggg gtaaagctaa attaaaagat gtcttacgtg tagcccggga ttgtggagcg     300
actcatgtct gtggaattct ctatagtgca tttcaaaaat atgcagttcc tacgaccgca     360
agaggtgtcg ccatggccgc ggacattta ggacaggtag ctgatactgc agcacaatac      420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgaatct catcgtggtt accctgggttc cggaaacgtc     660 gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagatggccg cgatctagct agtcacgcct agcatatac tcgtgtccag     840 ttaaaatctg ctcaagaagc cctaaaacaa gccgagcgca gtcgcttacc gtgataa        897

<210> SEQ ID NO 72
<211> LENGTH: 297
<212> TYPE: PRT
<213> ORGANISM: Artificial Sequence
<220> FEATURE:
<223> OTHER INFORMATION: variant 261746

<400> SEQUENCE: 72

Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu

```
              35                  40                  45
Phe Thr Arg Arg Glu Leu Glu Arg His Gly Leu Gly Val Thr Phe Ser
 50                  55                  60

Leu Gly Leu Asp Ala Gln Thr Asp Ile Ser Ser Gly Asp Pro Glu Arg
 65                  70                  75                  80

Ala Ala Arg Gly Lys Ala Lys Leu Asp Asp Val Leu Arg Val Ala Arg
                 85                  90                  95

Asp Cys Gly Gly Thr His Val Cys Gly Ile Leu Tyr Ser Ala Phe Gln
                100                 105                 110

Lys Asn Ala Val Pro Thr Thr Arg Ala Gly Val Ala Met Ala Ala Asp
                115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
                180                 185                 190

Ser Ala Ile Arg Asp Thr Gly Asp Arg Leu Gly Tyr Phe His Leu Gly
    195                 200                 205

Asp Ser His Arg Gly Tyr Leu Gly Ser Gly Asn Val Asp Phe Thr Ala
210                 215                 220

Val Phe Arg Ala Leu Arg Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
                260                 265                 270

Ala Leu Ala Tyr Thr Arg Val Gln Leu Lys Ser Ala Gln Glu Ala Leu
    275                 280                 285

Lys Gln Ala Glu Arg Ser Arg Leu Pro
290                 295

<210> SEQ ID NO 73
<211> LENGTH: 897
<212> TYPE: DNA
<213> ORGANISM: Artificial Sequence
<220> FEATURE:
<223> OTHER INFORMATION: coding sequence for variant 261747

<400> SEQUENCE: 73
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccgagaa gcattgatgc agagtttact cgcagagagt tagaaaaaca tgggttggga     180
gtaacctttt cgcttggact cgatgcgcaa acagacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaat atgcagttcc tacgaccgca     360
agaggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacggcagac     600
```

```
aggctagggt atttccatat tggcgattct catcgtggtt acctgggttc cggaaacgtc      660
gactttactg ccgtatttag ggcgctggta ttttctggat atacgggacc gattacattt      720
gagtcattct ccagtagagt cgtaggacaa ccattagagg gaattctggc aatttggcgt      780
aatttatggg aagatggccg cgatctagct agtcacgcct tagcatttac tcgtgtccag      840
ttaaaatctg ctcaagaagc cctaaaacaa gccgagcgca gtcgcttacc gtgataa         897
```

<210> SEQ ID NO 74
<211> LENGTH: 297
<212> TYPE: PRT
<213> ORGANISM: Artificial Sequence
<220> FEATURE:
<223> OTHER INFORMATION: variant 261747

<400> SEQUENCE: 74

Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Ser Asn Leu Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Ala Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Leu Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

<210> SEQ ID NO 75
<211> LENGTH: 897
<212> TYPE: DNA
<213> ORGANISM: Artificial Sequence
<220> FEATURE:
<223> OTHER INFORMATION: coding sequence for variant 261748

<400> SEQUENCE: 75

```
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaaaaata tgggttggga     180
gtaaccttt cgcttggact cgatgcgcaa acagacatta gttctggtga tccggaacgc      240
gcagcgcggg gtaaagctaa attaaaagat gtcttacgtg tagcccggga ttgtggagcg     300
actcatgtct gtggaattct ctatagtgca tttcaaaaat atgcagttcc tacgacccgt     360
agaggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgaatct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagattcacg cgatctagct agtcacgcct tagcatttac tcgtgtccag     840
ttaaaatctg ctcaagaagc cctaaaacaa gccgagcgca gtcgcttacc gtgataa       897
```

<210> SEQ ID NO 76
<211> LENGTH: 297
<212> TYPE: PRT
<213> ORGANISM: Artificial Sequence
<220> FEATURE:
<223> OTHER INFORMATION: variant 261748

<400> SEQUENCE: 76

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Ser Tyr Val Leu Asn Thr Ala
145                 150                 155                 160
```

-continued

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Leu Asp Phe Thr Ala
    210                 215                 220

Val Phe Arg Ala Leu Val Phe Ser Gly Tyr Thr Gly Pro Ile Thr Val
225                 230                 235                 240

Glu Ser Phe Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

<210> SEQ ID NO 77
<211> LENGTH: 897
<212> TYPE: DNA
<213> ORGANISM: Artificial Sequence
<220> FEATURE:
<223> OTHER INFORMATION: coding sequence for variant 261749

<400> SEQUENCE: 77
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccgagaa gcattgatgc agagtttact cgcagagagt tagaaaaaca tgggttggga     180
gtaacctttt cgcttggact cgatgcgcaa acagacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaat atgcagttcc tacgacccgt     360
agaggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacggcagac     600
aggctagggt atttccatat tggcgattct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagattcacg cgatctagct agtcacgcct tagcatttac tcgtgtccag     840
ttaaaatctg ctcaagaagc cctaaaacaa gccgagcgca gtcgcttacc gtgataa         897

<210> SEQ ID NO 78
<211> LENGTH: 297
<212> TYPE: PRT
<213> ORGANISM: Artificial Sequence
<220> FEATURE:
<223> OTHER INFORMATION: variant 261749

<400> SEQUENCE: 78

Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Leu His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Ile Phe Arg Ala Leu Val Phe Ser Gly Tyr Thr Gly Pro Ile Thr Leu
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

<210> SEQ ID NO 79
<211> LENGTH: 897
<212> TYPE: DNA
<213> ORGANISM: Artificial Sequence
<220> FEATURE:
<223> OTHER INFORMATION: coding sequence for variant 261750

<400> SEQUENCE: 79
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccgagaa gcattgatgc agattttact cgcagagagt tagaaaaaca tgggttggga     180 gtaaccttt cgcttggact cgatgcgcaa tgcgacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaat atgcagttcc tacgacccgt     360
agaggtgtcg ccatggccgc ggacatttta ggacaggtag ctgatactgc agcacaatac     420

-continued

```
ggtattactt tggggttaga agtcgttaac cgttatgaga caaatgtatt gaacaccgcg    480
tcacagggtg ttgaacttat tgagcgtatt ggtcgtccca acgtaaaagt gcatttagat    540
acgtatcaca tgaatattga agagagcgat attatgagcg cgatcagaga tacgggagac    600
aggctagggt atttccatat tggcgaatct catcgtggtt acctgggttc cggaaacgtc    660
gactttactg ccgtatttag ggcgctggta ttttctggat atacgggacc gattacattt    720
gagtcattct ccagtagagt cgtaggacaa ccattagagg gaattctggc aatttggcgt    780
aatttatggg aagatggccg cgatctagct agtcacgcct agcatatac tcgtgtccag    840 ttaaaatctg ctcaagaagc cctaaaacaa gccgagcgca gtcgcttacc gtgataa      897
```

<210> SEQ ID NO 80
<211> LENGTH: 297
<212> TYPE: PRT
<213> ORGANISM: Artificial Sequence
<220> FEATURE:
<223> OTHER INFORMATION: variant 261750

<400> SEQUENCE: 80

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Val Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Val Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Gly Leu Ala Tyr Thr Arg Val Gln Leu Lys Ser Ala Gln Glu Ala Leu
        275                 280                 285
```

Lys Gln Ala Glu Arg Ser Arg Leu Pro
              290                 295

<210> SEQ ID NO 81
<211> LENGTH: 897
<212> TYPE: DNA
<213> ORGANISM: Artificial Sequence
<220> FEATURE:
<223> OTHER INFORMATION: coding sequence for variant 261751

<400> SEQUENCE: 81
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agattttact cgcagagagt tagaaaaaca tgggttggga     180 gtaaccttt cgcttggact cgatgcgcaa tgcgacatta gttctggtga tccggaacgc      240
gcagcgcggg gtaaagctaa attaaaagat gtcttacgtg tagcccggga ttgtggagcg     300
actcatgtct gtggaattct ctatagtgca tttcaaaaat atgcagttcc tacgacccgt     360
agaggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgaatct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagatggccg cgatctagct agtcacgcct agcatttac tcgtgtccag      840 ttaaaatctg ctcaagaagc cctaaaacaa gccgagcgca gtcgcttacc gtgataa        897

<210> SEQ ID NO 82
<211> LENGTH: 297
<212> TYPE: PRT
<213> ORGANISM: Artificial Sequence
<220> FEATURE:
<223> OTHER INFORMATION: variant 261751

<400> SEQUENCE: 82

Met Asn Lys Leu Gly Val His Ala Leu Val Trp Glu Ala Gly Trp Ser
1               5                  10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu

```
                130             135             140
Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Thr Gly His Val Asp Phe Thr Ala
    210                 215                 220

Val Phe Arg Ala Leu Val Phe Ser Gly Tyr Thr Gly Pro Leu Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

<210> SEQ ID NO 83
<211> LENGTH: 897
<212> TYPE: DNA
<213> ORGANISM: Artificial Sequence
<220> FEATURE:
<223> OTHER INFORMATION: coding sequence for variant 261752

<400> SEQUENCE: 83
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccgagaa gcattgatgc agattttact cgcagagagt tagaaaaaca tgggttggga     180
gtaaccttt cgcttggact cgatgcgcaa tgcgacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaat atgcagttcc tacgaccgca     360
agaggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgattct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagatggccg cgatctagct agtcacgcct tagcatatac tcgtgtccag     840
ttaaaatctg ctcaagaagc cctaaaacaa gccgagcgca gtcgcttacc gtgataa      897

<210> SEQ ID NO 84
<211> LENGTH: 297
<212> TYPE: PRT
<213> ORGANISM: Artificial Sequence
<220> FEATURE:
<223> OTHER INFORMATION: variant 261752
```

-continued

<400> SEQUENCE: 84

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Phe Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Leu Asp Phe Thr Ala
    210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Leu Arg Val Gln Leu Lys Ser Ala Gln Glu Ala Leu
        275                 280                 285

Lys Gln Ala Glu Arg Ser Arg Leu Pro
    290                 295
```

<210> SEQ ID NO 85
<211> LENGTH: 897
<212> TYPE: DNA
<213> ORGANISM: Artificial Sequence
<220> FEATURE:
<223> OTHER INFORMATION: coding sequence for variant 261753

<400> SEQUENCE: 85

```
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaaaaata tgggttggga     180 gtaaccttt cgcttggact cgatgcgcaa tgcgacatta gttctggtga tccggaacgc     240
gcagcgcggg gtaaagctaa attaaagat gtcttacgtg tagcccggga ttgtggagcg     300
```

```
actcatgtct gtggaattct ctatagtgca tttcaaaaat atgcagttcc tacgacccgt    360
agaggtgtcg ccatggccgc ggacatttta ggacaggtag ctgatactgc agcacaatac    420
ggtattactt tggggttaga agtcgttaac cgttatgaga caaatgtatt gaacaccgcg    480
tcacagggtg ttgaacttat tgagcgtatt ggtcgtccca acgtaaaagt gcatttagat    540
acgtatcaca tgaatattga agagagcgat attatgagcg cgatcagaga tacggcagac    600
aggctagggt atttccatat tggcgattct catcgtggtt acctgggttc cggaaacgtc    660
gactttactg ccgtatttag ggcgctggta ttttctggat atacgggacc gattacattt    720
gagtcattct ccagtagagt cgtaggacaa ccattagagg gaattctggc aatttggcgt    780
aatttatggg aagattcacg cgatctagct agtcacgcct tagcatatac tcgtgtccag    840
ttaaaatctg ctcaagaagc cctaaaacaa gccgagcgca gtcgcttacc gtgataa       897
```

<210> SEQ ID NO 86
<211> LENGTH: 297
<212> TYPE: PRT
<213> ORGANISM: Artificial Sequence
<220> FEATURE:
<223> OTHER INFORMATION: variant 261753

<400> SEQUENCE: 86

```
Met Asn Lys Leu Gly Val His Ala Leu Val Trp Glu Ala Gly Trp Ser
 1               5                  10                  15

Arg Asp Glu Cys Ala Arg Ala Ile Ala Arg Thr Ala Glu Thr Gly Phe
            20                  25                  30

Asp Phe Ile Glu Leu Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
           100                 105                 110

Lys Asn Ala Val Pro Thr Thr Arg Ala Gly Val Ala Met Ala Ala Asp
       115                 120                 125

Ile Leu Gly Gln Val Ala Asp Thr Ala Ala Gln Tyr Gly Val Thr Leu
   130                 135                 140

Gly Leu Glu Val Val Asn Arg Tyr Glu Ser Asn Leu Leu Asn Thr Ala
145                 150                 155                 160

Ser Gln Gly Val Glu Leu Cys Glu Arg Ile Gly Arg Pro Asn Val Lys
               165                 170                 175

Val His Leu Asp Thr Tyr His Met Asn Ile Glu Glu Ser Asp Ile Met
           180                 185                 190

Ser Ala Ile Arg Asp Thr Gly Asp Arg Leu Gly Tyr Phe His Ile Gly
       195                 200                 205

Asp Ser His Arg Gly Tyr Leu Gly Ser Gly Asn Val Asp Phe Thr Ala
   210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
               245                 250                 255
```

```
Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

<210> SEQ ID NO 87
<211> LENGTH: 897
<212> TYPE: DNA
<213> ORGANISM: Artificial Sequence
<220> FEATURE:
<223> OTHER INFORMATION: coding sequence for variant 261754

<400> SEQUENCE: 87
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaaaaata tgggttggga     180
gtaacctttt cgcttggact cgatgcgcaa acagacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaat atgcagttcc tacgaccgca     360
agaggtgtcg ccatggccgc ggacatttta ggacaggtag ctgatactgc agcacaatac     420
ggtattactt tggggttaga agtcgttaac cgttatgaga caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacggcagac     600
aggctagggt atttccatat tggcgattct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagattcacg cgatctagct agtcacgcct agcatatac tcgtgtccag     840
ttaaaatctg ctcaagaagc cctaaaacaa gccgagcgca gtcgcttacc gtgataa       897

<210> SEQ ID NO 88
<211> LENGTH: 297
<212> TYPE: PRT
<213> ORGANISM: Artificial Sequence
<220> FEATURE:
<223> OTHER INFORMATION: variant 261754

<400> SEQUENCE: 88

Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110
```

```
Lys Asn Ala Val Pro Thr Thr Arg Ala Gly Val Ala Met Ala Ala Asp
            115                 120                 125

Ile Leu Gly Gln Val Ala Asp Thr Ala Ala Gln Tyr Gly Ile Thr Leu
        130                 135                 140

Gly Leu Glu Val Val Asn Arg Tyr Glu Ser Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Met
225                 230                 235                 240

Glu Cys Phe Ser Ser Arg Val Val Gly Gln Pro Leu Glu Gly Ile Leu
                245                 250                 255

Ala Ile Trp Arg Asn Leu Trp Glu Asp Ser Arg Asp Val Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
290                 295
```

<210> SEQ ID NO 89
<211> LENGTH: 897
<212> TYPE: DNA
<213> ORGANISM: Artificial Sequence
<220> FEATURE:
<223> OTHER INFORMATION: coding sequence for variant 277285

<400> SEQUENCE: 89

```
atgaataagt taggtgtgca cgcattagtt tgggaagcgg gttggagtcg tgatgagtgt    60
gctcgtgcca tcgcacgcac cgcggaaacg ggatttgact tcattgaagt cccagcgtta   120
gatccggcaa gcattgatgc agagtttact cgcagagagt tagaacgcca tgggttggga   180
gtaaccttt cgcttggact cgatgcgcaa acagacatta gttctggtga tccggaacgc   240
gcagcgcggg gtaaagctaa attaaaagat gtcttacgtg tagcccggga ttgtggagcg   300
actcatgtct gtggaattct ctatagtgca tttcaaaaaa atgcagttcc tacgacccgt   360
gcgggtgtcg ccatggccgc ggacattta ggacaggtag ctgatactgc agcacaatac   420
ggtattactt tggggttaga agtcgttaac cgttatgagt caaatgtatt gaacaccgcg   480
tcacagggtg ttgaactttg cgagcgtatt ggtcgtccca acgtaaaagt gcatttagat   540
acgtatcaca tgaatattga agagagcgat attatgagcg cgatcagaga tacgggagac   600
aggctagggt atttccatat tggcgattct catcgtggtt acctgggttc cggaaacgtc   660
gactttactg ccgtatttag ggcgctggta ttttctggat atacgggacc gattacattt   720
gagtcattct ccagtagagt cgtaggacaa ccattagagg gaattctggc aatttggcgt   780
aatttatggg aagattcccg cgatctagct agtcacgcct agcatatac tcgtgtccag   840
ttaaaatctg ctcaagaagc cctaaaacaa gccgagcgca gtcgcttacc gtgataa      897
```

<210> SEQ ID NO 90

<211> LENGTH: 297
<212> TYPE: PRT
<213> ORGANISM: Artificial Sequence
<220> FEATURE:
<223> OTHER INFORMATION: variant 277285

<400> SEQUENCE: 90

```
Met Asn Lys Leu Gly Val His Ala Leu Val Trp Glu Ala Gly Trp Ser
1               5                   10                  15
Arg Asp Glu Cys Ala Arg Ala Ile Ala Arg Thr Ala Glu Thr Gly Phe
            20                  25                  30
Asp Phe Ile Glu Val Pro Ala Leu Asp Pro Ala Ser Ile Asp Ala Glu
        35                  40                  45
Phe Thr Arg Arg Glu Leu Glu Arg His Gly Leu Gly Val Thr Phe Ser
    50                  55                  60
Leu Gly Leu Asp Ala Gln Thr Asp Ile Ser Ser Gly Asp Pro Glu Arg
65                  70                  75                  80
Ala Ala Arg Gly Lys Ala Lys Leu Lys Asp Val Leu Arg Val Ala Arg
                85                  90                  95
Asp Cys Gly Ala Thr His Val Cys Gly Ile Leu Tyr Ser Ala Phe Gln
            100                 105                 110
Lys Asn Ala Val Pro Thr Thr Arg Ala Gly Val Ala Met Ala Ala Asp
        115                 120                 125
Ile Leu Gly Gln Val Ala Asp Thr Ala Ala Gln Tyr Gly Ile Thr Leu
    130                 135                 140
Gly Leu Glu Val Val Asn Arg Tyr Glu Ser Asn Val Leu Asn Thr Ala
145                 150                 155                 160
Ser Gln Gly Val Glu Leu Cys Glu Arg Ile Gly Arg Pro Asn Val Lys
                165                 170                 175
Val His Leu Asp Thr Tyr His Met Asn Ile Glu Glu Ser Asp Ile Met
            180                 185                 190
Ser Ala Ile Arg Asp Thr Gly Asp Arg Leu Gly Tyr Phe His Ile Gly
        195                 200                 205
Asp Ser His Arg Gly Tyr Leu Gly Ser Gly Asn Val Asp Phe Thr Ala
    210                 215                 220
Val Phe Arg Ala Leu Val Phe Ser Gly Tyr Thr Gly Pro Ile Thr Phe
225                 230                 235                 240
Glu Ser Phe Ser Ser Arg Val Val Gly Gln Pro Leu Glu Gly Ile Leu
                245                 250                 255
Ala Ile Trp Arg Asn Leu Trp Glu Asp Ser Arg Asp Leu Ala Ser His
            260                 265                 270
Ala Leu Ala Tyr Thr Arg Val Gln Leu Lys Ser Ala Gln Glu Ala Leu
        275                 280                 285
Lys Gln Ala Glu Arg Ser Arg Leu Pro
    290                 295
```

<210> SEQ ID NO 91
<211> LENGTH: 897
<212> TYPE: DNA
<213> ORGANISM: Artificial Sequence
<220> FEATURE:
<223> OTHER INFORMATION: coding sequence for variant 277286

<400> SEQUENCE: 91

```
atgaataagt taggtgtgca cgcattagtt tgggaagcgg gttggagtcg tgatgagtgt     60
gctcgtgcca tcgcacgcac cgcggaaacg ggatttgact tcattgaagt cccagcgtta    120
```

```
gatccggcaa gcattgatgc agagtttact cgcagagagt tagaacgcca tgggttggga    180 gtaaccttt  cgcttggact cgatgcgcaa acagacatta gttctggtga tccggaacgc    240
gcagcgcggg gtaaagctaa attagacgat gtcttacgtg tagcccggga ttgtggagcg    300
actcatgtct gtggaattct ctatagtgca tttcaaaaaa atgcagttcc tacgacccgt    360
gcgggtgtcg ccatggccgc ggacatttta ggacaggtag ctgatactgc agcacaatac    420
ggtattactt tggggttaga agtcgttaac cgttatgaga caaatgtatt gaacaccgcg    480
tcacagggtg ttgaactttg cgagcgtatt ggtcgtccca acgtaaaagt gcatttagat    540
acgtatcaca tgaatattga agagagcgat attatgagcg cgatcagaga tacgggagac    600
aggctagggt atttccatat tggcgattct catcgtggtt acctgggttc cggaaacgtc    660
gactttactg ccgtatttag ggcgctggta ttttctggat atacgggacc gattacattt    720
gagtcattct ccagtagagt cgtaggacaa ccattagagg gaattctggc aatttggcgt    780
aatttatggg aagattcccg cgatctagct agtcacgcct agcatatac tcgtgtccag    840 ttaaaatctg ctcaagaagc cctaaaacaa gccgagcgca gtcgcttacc gtgataa      897
```

<210> SEQ ID NO 92
<211> LENGTH: 297
<212> TYPE: PRT
<213> ORGANISM: Artificial Sequence
<220> FEATURE:
<223> OTHER INFORMATION: variant 277286

<400> SEQUENCE: 92

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Thr Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Phe
```

```
                        225                 230                 235                 240
Glu Ser Phe Ser Ser Arg Val Val Gly Gln Pro Leu Glu Gly Ile Leu
                    245                 250                 255

Ala Ile Trp Arg Asn Leu Trp Glu Asp Ser Arg Asp Leu Ala Ser His
                260                 265                 270

Ala Leu Ala Tyr Thr Arg Val Gln Leu Lys Ser Ala Gln Glu Ala Leu
            275                 280                 285

Lys Gln Ala Glu Arg Ser Arg Leu Pro
        290                 295

<210> SEQ ID NO 93
<211> LENGTH: 897
<212> TYPE: DNA
<213> ORGANISM: Artificial Sequence
<220> FEATURE:
<223> OTHER INFORMATION: coding sequence for variant 277287

<400> SEQUENCE: 93
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaacgcca tgggttggga     180 gtaaccttt cgcttggact cgatgcgcaa acagacatta gttctggtga tccggaacgc     240
gcagcgcggg gtaaagctaa attagacgat gtcttacgtg tagcccggga ttgtggagcg     300
actcatgtct gtggaattct ctatagtgca tttcaaaaaa atgcagttcc tacgacccgt     360
gcgggtgtcg ccatggccgc ggacatttta ggacaggtag ctgatactgc agcacaatac     420
ggtattactt tggggttaga agtcgttaac cgttatgagt caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgattct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagattcccg cgatctagct agtcacgcct agcatatac tcgtgtccag     840 ttaaaatctg ctcaagaagc cctaaaacaa gccgagcgca gtcgcttacc gtgataa       897

<210> SEQ ID NO 94
<211> LENGTH: 297
<212> TYPE: PRT
<213> ORGANISM: Artificial Sequence
<220> FEATURE:
<223> OTHER INFORMATION: variant 277287

<400> SEQUENCE: 94

Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80
```

```
Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Ser Asn Val Leu Asn Thr Ala
145                 150                 155                 160

Ser Gln Gly Val Glu Leu Ile Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

<210> SEQ ID NO 95
<211> LENGTH: 897
<212> TYPE: DNA
<213> ORGANISM: Artificial Sequence
<220> FEATURE:
<223> OTHER INFORMATION: coding sequence for variant 277288

<400> SEQUENCE: 95
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaacgcca tgggttggga     180 gtaaccttt  cgcttggact cgatgcgcaa acagacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaaa atgcagttcc tacgacccgt     360
gcgggtgtcg ccatggccgc ggacatttta gacaggtag  ctgatactgc agcacaatac     420
ggtattactt tggggttaga agtcgttaac cgttatgaga caaatgtatt gaacaccgcg     480
tcacagggtg ttgaactttg cgagcgtatt ggtcgtccca acgtaaaagt gcatttagat     540
acgtatcaca tgaatattga agagagcgat attatgagcg cgatcagaga tacgggagac     600
aggctagggt atttccatat tggcgattct catcgtggtt acctgggttc cggaaacgtc     660
gactttactg ccgtatttag ggcgctggta ttttctggat atacgggacc gattacattt     720
gagtcattct ccagtagagt cgtaggacaa ccattagagg gaattctggc aatttggcgt     780
aatttatggg aagattcccg cgatctagct agtcacgcct agcatatac  tcgtgtccag     840
```
ttaaaatctg ctcaagaagc cctaaaacaa gccgagcgca gtcgcttacc gtgataa       897

<210> SEQ ID NO 96
<211> LENGTH: 297
<212> TYPE: PRT
<213> ORGANISM: Artificial Sequence
<220> FEATURE:
<223> OTHER INFORMATION: variant 277288

<400> SEQUENCE: 96

Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Lys Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Thr Asn Val Leu Asn Thr Ala
145                 150                 155                 160

Ser Gln Gly Val Glu Leu Cys Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

<210> SEQ ID NO 97
<211> LENGTH: 897
<212> TYPE: DNA
<213> ORGANISM: Artificial Sequence
<220> FEATURE:
<223> OTHER INFORMATION: coding sequence for variant 277289

<400> SEQUENCE: 97

```
atgaataagt taggtgtgca cgcattagtt tgggaagcgg gttggagtcg tgatgagtgt    60
gctcgtgcca tcgcacgcac cgcggaaacg ggatttgact tcattgaagt cccagcgtta   120
gatccggcaa gcattgatgc agagtttact cgcagagagt tagaacgcca tgggttggga   180
gtaacctttt cgcttggact cgatgcgcaa acagacatta gttctggtga tccggaacgc   240
gcagcgcggg gtaaagctaa attagacgat gtcttacgtg tagcccggga ttgtggagcg   300
actcatgtct gtggaattct ctatagtgca tttcaaaaaa atgcagttcc tacgacccgt   360
gcgggtgtcg ccatggccgc ggacatttta ggacaggtag ctgatactgc agcacaatac   420
ggtattactt tggggttaga agtcgttaac cgttatgaga caaatgtatt gaacaccgcg   480
tcacagggtg ttgaacttat tgagcgtatt ggtcgtccca acgtaaaagt gcatttagat   540
acgtatcaca tgaatattga agagagcgat attatgagcg cgatcagaga tacgggagac   600
aggctagggt atttccatat tggcgattct catcgtggtt acctgggttc cggaaacgtc   660
gactttactg ccgtatttag ggcgctggta ttttctggat atacgggacc gattacattt   720
gagtcattct ccagtagagt cgtaggacaa ccattagagg gaattctggc aatttggcgt   780
aatttatggg aagattcccg cgatctagct agtcacgcct tagcatatac tcgtgtccag   840
ttaaaatctg ctcaagaagc cctaaaacaa gccgagcgca gtcgcttacc gtgataa       897
```

<210> SEQ ID NO 98  
<211> LENGTH: 297  
<212> TYPE: PRT  
<213> ORGANISM: Artificial Sequence  
<220> FEATURE:  
<223> OTHER INFORMATION: variant 277289

<400> SEQUENCE: 98

```
Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
            20                  25                  30

Asp Phe Ile Glu Val Pro Ala Leu Asp Pro Ala Ser Ile Asp Ala Glu
        35                  40                  45

Phe Thr Arg Arg Glu Leu Glu Arg His Gly Leu Gly Val Thr Phe Ser
    50                  55                  60

Leu Gly Leu Asp Ala Gln Thr Asp Ile Ser Ser Gly Asp Pro Glu Arg
65                  70                  75                  80

Ala Ala Arg Gly Lys Ala Lys Leu Asp Asp Val Leu Arg Val Ala Arg
                85                  90                  95

Asp Cys Gly Ala Thr His Val Cys Gly Ile Leu Tyr Ser Ala Phe Gln
            100                 105                 110

Lys Asn Ala Val Pro Thr Thr Arg Ala Gly Val Ala Met Ala Ala Asp
        115                 120                 125

Ile Leu Gly Gln Val Ala Asp Thr Ala Ala Gln Tyr Gly Ile Thr Leu
    130                 135                 140

Gly Leu Glu Val Val Asn Arg Tyr Glu Thr Asn Val Leu Asn Thr Ala
145                 150                 155                 160

Ser Gln Gly Val Glu Leu Ile Glu Arg Ile Gly Arg Pro Asn Val Lys
                165                 170                 175

Val His Leu Asp Thr Tyr His Met Asn Ile Glu Glu Ser Asp Ile Met
            180                 185                 190

Ser Ala Ile Arg Asp Thr Gly Asp Arg Leu Gly Tyr Phe His Ile Gly
        195                 200                 205
```

Asp Ser His Arg Gly Tyr Leu Gly Ser Gly Asn Val Asp Phe Thr Ala
    210                 215                 220

Val Phe Arg Ala Leu Val Phe Ser Gly Tyr Thr Gly Pro Ile Thr Phe
225                 230                 235                 240

Glu Ser Phe Ser Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
            260                 265                 270

Ala Leu Ala Tyr Thr Arg Val Gln Leu Lys Ser Ala Gln Glu Ala Leu
        275                 280                 285

Lys Gln Ala Glu Arg Ser Arg Leu Pro
    290                 295

<210> SEQ ID NO 99
<211> LENGTH: 897
<212> TYPE: DNA
<213> ORGANISM: Artificial Sequence
<220> FEATURE:
<223> OTHER INFORMATION: coding sequence for variant 277290

<400> SEQUENCE: 99
atgaataagt taggtgtgca cgcattagtt tgggaagcgg gttggagtcg tgatgagtgt      60
gctcgtgcca tcgcacgcac cgcggaaacg ggatttgact tcattgaagt cccagcgtta     120
gatccggcaa gcattgatgc agagtttact cgcagagagt tagaacgcca tgggttggga     180
gtaacctttt cgcttggact cgatgcgcaa acagacatta gttctggtga tccggaacgc     240
gcagcgcggg gtaaagctaa attaaaagat gtcttacgtg tagcccggga ttgtggagcg     300
actcatgtct gtggaattct ctatagtgca tttcaaaaaa atgcagttcc tacgacccgt     360
gcgggtgtcg ccatggccgc ggacatttta ggacaggtag ctgatactgc agcacaatac     420
ggtattactt tggggttaga agtcgttaac cgttatgagt caaatgtatt gaacaccgcg     480
tcacagggtg ttgaacttat tgagcgtatt ggtcgtccca acgtaaaagt gcatttagat     540
acgtatcaca tgaatattga agagagcgat attatgagcg cgatcagaga tacgggagac     600
aggctagggt atttccatat tggcgattct catcgtggtt acctgggttc cggaaacgtc     660
gactttactg ccgtatttag ggcgctggta ttttctggat atacgggacc gattacattt     720
gagtcattct ccagtagagt cgtaggacaa ccattgaggg aattctggc aatttggcgt      780
aatttatggg aagattcccg cgatctagct agtcacgcct tagcatatac tcgtgtccag     840
ttaaaatctg ctcaagaagc cctaaaacaa gccgagcgca gtcgcttacc gtgataa        897

<210> SEQ ID NO 100
<211> LENGTH: 297
<212> TYPE: PRT
<213> ORGANISM: Artificial Sequence
<220> FEATURE:
<223> OTHER INFORMATION: variant 277290

<400> SEQUENCE: 100

Met Asn Lys Leu Gly Val His Ala Leu Val Trp Glu Ala Gly Trp Ser
1               5                   10                  15

Arg Asp Glu Cys Ala Arg Ala Ile Ala Arg Thr Ala Glu Thr Gly Phe
                20                  25                  30

Asp Phe Ile Glu Val Pro Ala Leu Asp Pro Ala Ser Ile Asp Ala Glu
            35                  40                  45

Phe Thr Arg Arg Glu Leu Glu Arg His Gly Leu Gly Val Thr Phe Ser

-continued

```
            50                  55                  60
Leu Gly Leu Asp Ala Gln Thr Asp Ile Ser Ser Gly Asp Pro Glu Arg
 65                  70                  75                  80

Ala Ala Arg Gly Lys Ala Lys Leu Lys Asp Val Leu Arg Val Ala Arg
                 85                  90                  95

Asp Cys Gly Ala Thr His Val Cys Gly Ile Leu Tyr Ser Ala Phe Gln
                100                 105                 110

Lys Asn Ala Val Pro Thr Thr Arg Ala Gly Val Ala Met Ala Ala Asp
             115                 120                 125

Ile Leu Gly Gln Val Ala Asp Thr Ala Ala Gln Tyr Gly Ile Thr Leu
         130                 135                 140

Gly Leu Glu Val Val Asn Arg Tyr Glu Ser Asn Val Leu Asn Thr Ala
145                 150                 155                 160

Ser Gln Gly Val Glu Leu Ile Glu Arg Ile Gly Arg Pro Asn Val Lys
                165                 170                 175

Val His Leu Asp Thr Tyr His Met Asn Ile Glu Glu Ser Asp Ile Met
             180                 185                 190

Ser Ala Ile Arg Asp Thr Gly Asp Arg Leu Gly Tyr Phe His Ile Gly
         195                 200                 205

Asp Ser His Arg Gly Tyr Leu Gly Ser Gly Asn Val Asp Phe Thr Ala
         210                 215                 220

Val Phe Arg Ala Leu Val Phe Ser Gly Tyr Thr Gly Pro Ile Thr Phe
225                 230                 235                 240

Glu Ser Phe Ser Arg Val Val Gly Gln Pro Leu Glu Gly Ile Leu
                245                 250                 255

Ala Ile Trp Arg Asn Leu Trp Glu Asp Ser Arg Asp Leu Ala Ser His
             260                 265                 270

Ala Leu Ala Tyr Thr Arg Val Gln Leu Lys Ser Ala Gln Glu Ala Leu
         275                 280                 285

Lys Gln Ala Glu Arg Ser Arg Leu Pro
         290                 295
```

EPIMERASE ENZYMES AND THEIR USE

CROSS-REFERENCE TO RELATED APPLICATIONS

This application is a national stage entry of International Application No. PCT/US19/45400, filed Aug. 7, 2019, which itself claims priority to U.S. Provisional Patent Application No. 62/716,204, filed Aug. 8, 2018, the contents of each are incorporated herein by reference.

Each reference, patent, and published patent application cited in this disclosure is incorporated herein by reference in its entirety.

This application incorporates by reference a 179 kb text file created on Jan. 5, 2022, and named "FINALCP0178sequencelisting-revised2" which is the sequence listing for this application.

TECHNICAL FIELD

This disclosure relates generally to the production of allulose.

DETAILED DESCRIPTION

Figure 1:
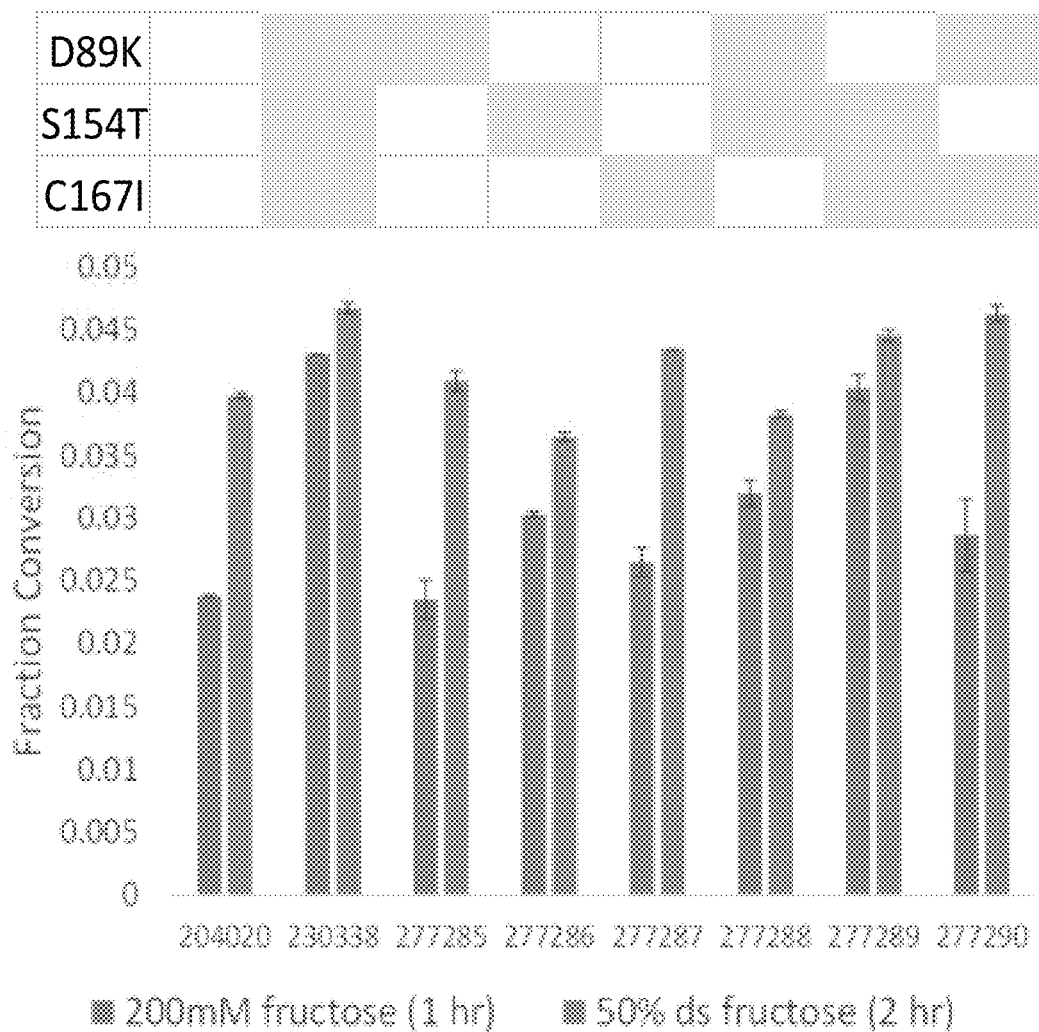
FIG. 1. Graph showing the effect of amino acid substitution on fraction of fructose converted by wild-type epimerase (204020, SEQ ID NO:6) and by epimerase variants 230338 (SEQ ID NO:16), 277285 (SEQ ID NO:90), 277286 (SEQ ID NO:92), 277287 (SEQ ID NO:94), 277288 (SEQ ID NO:96), 277289 (SEQ ID NO:98), and 277290 (SEQ ID NO:100). Left bar of each pair, 200 mM; right bar of each pair, 50% (w/w).

This disclosure provides epimerase enzymes useful for commercial scale production of allulose from fructose. The disclosed enzymes ("epimerase variants") are variants of *Burkholderia multivorans* CGD1 xylose isomerase (SEQ ID NO:6) engineered to have improved catalytic activity of about 1.5- to 2-fold compared with the parent enzyme. Table 1 below identifies the amino acid sequence of each epimerase variant in the accompanying sequence listing and provides an example of a nucleic acid sequence encoding the variant. The amino acid differences between each epimerase variant and the parent enzyme (SEQ ID NO:6) are summarized in Table 2, in which the amino acid numbers refer to those of SEQ ID NO:6.

TABLE 1

Amino Acid Sequences and Examples of Coding Sequences of Epimerase Variants

| Gene ID | SEQ ID NO: nucleotide | SEQ ID NO: protein |
|---|---|---|
| 230338 | 15 | 16 |
| 256407 | 17 | 18 |
| 257999 | 39 | 40 |
| 261731 | 41 | 42 |
| 261732 | 43 | 44 |
| 261733 | 45 | 46 |
| 261734 | 47 | 48 |
| 261735 | 49 | 50 |
| 261736 | 51 | 52 |
| 261737 | 53 | 54 |
| 261738 | 55 | 56 |
| 261739 | 57 | 58 |
| 261740 | 59 | 60 |
| 261741 | 61 | 62 |
| 261742 | 63 | 64 |
| 261743 | 65 | 66 |
| 261744 | 67 | 68 |
| 261745 | 69 | 70 |
| 261746 | 71 | 72 |
| 261747 | 73 | 74 |
| 261748 | 75 | 76 |
| 261749 | 77 | 78 |
| 261750 | 79 | 80 |
| 261751 | 81 | 82 |
| 261752 | 83 | 84 |
| 261753 | 85 | 86 |
| 261754 | 87 | 88 |
| 277285 | 89 | 90 |
| 277286 | 91 | 92 |
| 277287 | 93 | 94 |
| 277288 | 95 | 96 |
| 277289 | 97 | 98 |
| 277290 | 99 | 100 |

TABLE 2

Epimerase Variants

| Gene ID | Amino Acid Variations of SEQ ID NO: 6 | | | | | | | | | | |
|---|---|---|---|---|---|---|---|---|---|---|---|
| 230338 | | | D89K | | | | S154T | C167I | | | |
| 256407 | | | D89K F111L | N114Y | R120A | A121D | S154T | C167I | | | |
| 257999 | R56K | | D89K | N114Y | | A121R | S154T | C167I | | S266G | |
| 261731 | R56K | | D89K | N114Y | R120A | A121R | S154T | C167I G199A | D209E | S266G | Y276F |
| 261732 | R56K | T71C | D89K | N114Y | R120A | A121R | S154T | C167I | D209E | S266G | Y276F |
| 261733 | R56K | T71C | D89K | N114Y | R120A | A121R | S154T | C167I G199A | D209E | S266G | |
| 261734 | R56K | T71C | D89K | N114Y | R120A | A121R | S154T | C167I G199A | | S266G | Y276F |
| 261735 | R56K | T71C | D89K | N114Y | | A121R | S154T | C167I G199A | D209E | S266G | Y276F |
| 261736 | R56K | | D89K | N114Y | R120A | A121R | S154T | C167I | D209E | S266G | Y276F |
| 261737 | R56K | | D89K | N114Y | R120A | A121R | S154T | C167I G199A | D209E | S266G | |
| 261738 | R56K | T71C | D89K | N114Y | R120A | A121R | S154T | C167I | D209E | S266G | |
| 261739 | R56K | | D89K | N114Y | | A121R | S154T | C167I G199A | D209E | S266G | Y276F |
| 261740 | R56K | T71C | D89K | N114Y | | A121R | S154T | C167I | D209E | S266G | Y276F |
| 261741 | R56K | T71C | D89K | N114Y | | A121R | S154T | C167I G199A | | S266G | Y276F |

TABLE 2-continued

Epimerase Variants

Gene ID — Amino Acid Variations of SEQ ID NO: 6

| Gene ID | A43R | E48D | R56K | H57Y | T71C | D89K | N114Y | R120A | A121R | S154T | C167I | G199A | D209E | S266G | Y276F |
|---------|------|------|------|------|------|------|-------|-------|-------|-------|-------|-------|-------|-------|-------|
| 261742 |      |      | R56K |      |      | D89K | N114Y | R120A | A121R | S154T | C167I | G199A |       | S266G | Y276F |
| 261743 |      |      | R56K |      | T71C | D89K | N114Y | R120A | A121R | S154T | C167I |       |       | S266G | Y276F |
| 261744 |      |      | R56K |      | T71C | D89K | N114Y |       | A121R | S154T | C167I | G199A | D209E | S266G |       |
| 261745 |      |      | R56K |      | T71C | D89K | N114Y | R120A | A121R | S154T | C167I | G199A |       | S266G |       |
| 261746 |      | E48D | R56K | H57Y |      | D89K | N114Y | R120A | A121R | S154T | C167I |       | D209E | S266G |       |
| 261747 | A43R |      | R56K |      |      | D89K | N114Y | R120A | A121R | S154T | C167I | G199A |       | S266G | Y276F |
| 261748 |      |      | R56K | H57Y |      | D89K | N114Y |       | A121R | S154T | C167I |       | D209E |       | Y276F |
| 261749 | A43R |      | R56K |      |      | D89K | N114Y |       | A121R | S154T | C167I | G199A |       |       | Y276F |
| 261750 | A43R | E48D | R56K |      | T71C | D89K | N114Y |       | A121R | S154T | C167I |       | D209E | S266G |       |
| 261751 |      | E48D | R56K |      | T71C | D89K | N114Y |       | A121R | S154T | C167I |       | D209E | S266G | Y276F |
| 261752 | A43R | E48D | R56K |      | T71C | D89K | N114Y | R120A | A121R | S154T | C167I |       |       | S266G |       |
| 261753 |      |      | R56K | H57Y | T71C | D89K | N114Y |       | A121R | S154T | C167I | G199A |       |       |       |
| 261754 |      |      | R56K | H57Y |      | D89K | N114Y | R120A | A121R | S154T | C167I | G199A |       |       |       |
| 277285 |      |      |      |      |      | D89K |       |       |       |       |       |       |       |       |       |
| 277286 |      |      |      |      |      |      |       |       |       | S154T |       |       |       |       |       |
| 277287 |      |      |      |      |      |      |       |       |       |       | C167I |       |       |       |       |
| 277288 |      |      |      |      |      | D89K |       |       |       | S154T |       |       |       |       |       |
| 277289 |      |      |      |      |      |      |       |       |       | S154T | C167I |       |       |       |       |
| 277290 |      |      |      |      |      | D89K |       |       |       |       | C167I |       |       |       |       |

Nucleic Acids, Vectors, and Host Microorganisms

This disclosure provides nucleic acids encoding the disclosed epimerase variants described above. The sequence listing provides examples of nucleotide sequences encoding these variants, but any nucleotide sequence that encodes the epimerase variants can be used.

The nucleotide sequences can be optimized for expression in various species or strains of microorganisms as is well known in the art. Suitable microorganisms include, but are not limited to *Bacillus licheniformis, Saccharomyces cerevisiae, Schizosaccharomyces pombe, Pseudomonas putida, Pichia* sp., *Aspergillus* sp., *Trichoderma reesei, Corynebacterium glutamicum, E. coli*, and *B. subtilis*. Vectors containing promoters and other necessary regulatory sequences to express any protein in these organisms are known and readily available to those of ordinary skill in the art.

Nucleic acids encoding the epimerase variants described above can be included in vectors in which a coding sequence is operably linked to a suitable regulatory sequence for expression in a desired host microorganism. The regulatory sequence includes a suitable mRNA ribosome binding site and a sequence for regulating the termination of transcription and translation and may include other elements, such as a promoter or operator. Once transformed into a host microorganism, the vector may replicate or function independently of the host genome or may integrate into the genome itself. The vector that is used is not specifically limited and may be any vector known in the art, as long as it can replicate in the host.

A vector can include at least one selectable marker, such as an antibiotic resistance gene. Suitable antibiotics include, e.g., amikacin, ampicillin, augmentin (amoxicillin plus clavulonic acid), cefazolin, cefoxitin, ceftazidime, ceftiofur, cephalothin, chloramphenicol, enrofloxacin, florfenicol, gentamicin, imipenem, kanamycin, penicillin, sarafloxicin, spectinomycin, streptomycin, tetracycline, ticarcillin, and tilmicosin.

Vectors can be used to engineer a microorganism to produce one or more of the epimerase variants described above. Methods of delivering vectors to microorganisms are well known and include, for example, calcium phosphate transfection, DEAE-dextran mediated transfection, microinjection, lipid-mediated transfection, electroporation, conjugation, and infection.

Methods of Producing Allulose

The epimerase variants disclosed herein can be used for commercial scale production of allulose from fructose using methods well known in the art. See, for example, US 2017/0101637, US 2017/0298400, US 2016/0304853, and US 2016/0281076.

In some embodiments, an epimerase variant or an extract from a microorganism comprising the epimerase variant is bound to a solid matrix, and an input solution comprising fructose is passed over the matrix to convert at least a portion of the fructose to allulose, which can be recovered from the output stream. Optionally, the allulose can be separated from other components in the output stream and can be concentrated.

Many solid matrices suitable for binding enzymes are well known in the art and include alginate (e.g., sodium alginate), AMBERLITE™ resins (e.g., XAD®2, XAD®4, XAD®8, XAD®16 (Sigma Aldrich), SEPHADEX® resins or DUOLITE™ resins (e.g., A568; Dow Chemical); and Purolite CR8415 and ECR 8314 (Purolite). See also WO 2016/160573 and WO 2016/191267. Methods for immobilizing epimerases on a support and are well known to the person skilled in the art. See, for example, U.S. Pat. No. 8,375,106.

In other embodiments, a microorganism expressing an epimerase variant can be permeabilized and immobilized on alginate beads, as described in U.S. Pat. No. 8,735,106, or onto clays, carbon, diatomaceous earth, or a hydrogel such as polyacrylamide.

Those skilled in the art will appreciate that there are numerous variations and permutations of the above described embodiments that fall within the scope of the appended claims.

Example 1. Generation of a Marker-Free *Bacillus subtilis* Strain for Commercial Production of Allulose Epimerase This example describes the generation of a marker-free *B. subtilis* strain expressing allulose epimerase. Briefly, in a first step, a *B. subtilis* strain was transformed with a cassette encoding the BMCGD1 epimerase and including an antibiotic resistance marker. This cassette recombined into the *Bacillus* chromosome and knocked out 8 kb of DNA, including a large sporulation gene cluster and the lysine biosynthesis gene lysA. In a second step, a second cassette was recombined into the *B. subtilis* chromosome, restoring the lysA gene and removing DNA encoding the antibiotic resistance. *E. coli* strain 39 A10 from the Keio collection was used to passage plasmid DNA prior to transformation of *B. subtilis*. The relevant phenotype is a deficiency in the DNA methylase HsdM in an otherwise wild-type K-12 strain of *E. coli*.

In detail, a cassette of 5120 bp (SEQ ID NO:1; synthetic DNA from IDT, Coralville, Iowa) was synthesized and cloned into a standard ampicillin resistant pIDT vector. The synthetic piece encoded 700 bp upstream of lysA on the *B. subtilis* chromosome, the antibiotic marker cat (651 bp), the DNA-binding protein laI (1083 bp), and the allulose epimerase (894 bp), and included 700 bp of homology in dacF. This vector was transformed into *E. coli* strain 39 A10 (Baba et al., 2006), and plasmid DNA was prepared and transformed into *B. subtilis* strains 1A751 and 1A976.

Transformants were selected on LB supplemented with chloramphenicol. The replicon for pIDT is functional in *E. coli* but does not work in Gram positive bacteria such as *B. subtilis*. The colonies that arose therefore represented an integration event into the chromosome. In strain 1A751, the colony morphology on the plates was used to distinguish between single and double recombination events. The double recombination event would knock out genes required for sporulation, whereas the single recombination would not. After three days on LB plates, colonies capable of sporulation were brown and opaque; sporulation-deficient colonies were more translucent.

*B. subtilis* strain 1A976 with the allulose epimerase cassette is auxotrophic for histidine and lysine and can achieve very high transformation efficiency upon xylose induction. A 1925 bp synthetic DNA (SEQ ID NO:2) was amplified by primers (SEQ ID NO:3, SEQ ID NO:4) and Taq polymerase (Promega). This PCR product encoded the lysA gene that was deleted by the dropping in the epimerase cassette and 500 bp of homology to laI. A successful double recombination event of this DNA should result in colonies that are prototrophic for lysine and sensitive to chloramphenicol; i.e., the entire cat gene should be lost.

Transformants were selected on Davis minimal media supplemented with histidine. Colonies that arose were characterized by PCR and streaking onto LB with and without chloramphenicol. Strains that amplified the introduced DNA and that were chloramphenicol sensitive were further characterized, and their chromosomal DNA was extracted.

Strain 1A751 containing the chloramphenicol resistant allulose was transformed with this chromosomal DNA and selected on Davis minimal media supplemented with histidine. Transformants were streaked onto LB with and without chloramphenicol and characterized enzymatically as described below.

Example 2. Analysis of Epimerase Protein Levels

Epimerase protein levels in crude and soluble lysates were analyzed by polyacrylamide gel electrophoresis on 4-12% Bis-Tris NuPAGE (NUPAGE®) gels (Invitrogen). Protein levels were determined by densitometry of gels stained with SimplyBlue (SIMPLYBLUE™) Safe Stain (Invitrogen) using protein quantification standards.

Example 3. Expression of the BMCGD1 Epimerase in *B. subtilis*

A pHT254 construct harboring the BMCGD1 epimerase gene was codon optimized for expression in *B. subtilis* (SEQ ID NO:5) and used to transform *B. subtilis* strain DP1077. Strain DP1077 is a sporulation-defective (AspoIIG::ZeoR) derivative of the *Bacillus* Genetic Stock Center strain 1A976 (Em his nprE18 aprE3 eglS(DELTA)102 bglT/bglS (DELTA)EV lacA::PxylA-comK). In addition to being sporulation defective, the strain is defective in the ability to secrete neutral protease and subtilisin as a result of mutations in the nprE and aprE genes, respectively. The strain additionally bears an expression cassette placing the competence factor, comK, under the control of a xylose-inducible promoter for the simple production of competent cells.

Transformants were selected and cultured in either custom Azure media lacking $Mn^{2+}$ and $Co^{2+}$ (Teknova) supplemented with 1% glucose and 5 μg/ml chloramphenicol or in Davis minimal media (HiMedia) supplemented with 2 g/L synthetic complete amino acid mixture (MP Biomedicals), 1% glucose, and 5 μg/ml chloramphenicol. Cultures were grown at 37° C. for 16 h. Forty μL of this culture was used to inoculate 2 ml of fresh medium, and the resulting culture was incubated at 37° C. to mid-log growth (OD at 600 nm of ~0.7). The culture was then induced with 1 mM IPTG and incubation was continued at 37° C. for 4 hours or 24° C. for 20 h.

Cells were harvested by centrifugation, twice frozen and thawed, and lysed using the PeriPreps (PERIPREPS™) full lysis protocol (Epicentre). The soluble proteins in the lysates were prepared by collection of the supernatant fractions after centrifugation of the crude lysates.

Epimerase protein levels in crude and soluble lysates were analyzed by polyacrylamide gel electrophoresis as described above in Example 2.

Example 4. Generation of Epimerase Variants

Based on methods described in U.S. Pat. No. 8,635,029, nucleotide changes encoding amino acid variations were introduced into the BMCGD1 optimized coding sequence and used to generate coding sequences for epimerase variants. These coding sequences were engineered into pHT254 (MoBiTech, Inc.). This vector expresses a gene of interest from a strong Pgrac100 promoter which is derived from the promoter preceding the groESL operon of *Bacillus subtilis*. It contains improved regulatory elements fused to the lac operator allowing induction by IPTG and a strong ribosomal binding site. Nucleotides were optimized at the conserved regions of the groESL promoter including the UP element, the −35 and the −15 region (Phan et al., 2012). Each coding sequence was cloned into expression vector pHT254 at the BamHI and XmaI restriction sites.

The vectors were then transformed into *Bacillus subtilis* DB1077 strain as described above. Transformants were selected on LB agar media containing 5 μg/mL chloramphenicol.

Ninety-six *B. subtilis* transformants were picked to Davis minimal medium. Davis minimal medium was made by using reagent grade water and in a final volume of 1 L, 10.6 g Minimal Broth Davis w/o Dextrose (HIMEDIA cat. no. M390-500G) with 2 g of synthetic complete amino acid Mixture (MP Biomedicals cat. no. 4400-022) and autoclaved for 15 min at 121° C. Prior to use, glucose was added to 1%, and chloramphenicol was added to 5 µg/ml.

Example 5. Screening of Transformants for Epimerase Activity

For D-fructose to D-allulose epimerase screening, transformants were picked to 600 µL Davis minimal media (HiMedia) supplemented with 2 g/L synthetic complete amino acid (MP Biomedicals), 1% glucose, and 5 µg/mL chloramphenicol. Cells were grown to mid-log at 37° C., then induced with IPTG for 20 h at 24° C. Cells were harvested by centrifugation and lysed using the PeriPreps lysis protocol (Epicentre) in a final volume of 75 µL. Soluble protein expression was analyzed by polyacrylamide gel electrophoresis on 4-12% Bis-Tris NuPAGE gels (Invitrogen) and protein levels were determined by densitometry against quantitation standards. Soluble epimerase recovered ranged from 1-10 µg/mL of culture.

For epimerase activity of the *B. subtilis* derived lysates, reactions were assayed in a volume of 100 µL: 10% v/v clarified lysate, low (200 mM) or high (50% wt/wt) fructose, and 5 mM $MgCl_2$. Reactions were incubated at 70° C. for 2 h and stopped by addition of 10% volume 2% HCl and chilling to 4° C. Reactions were filtered through a PES membrane at a 10 kDa molecular weight cutoff (Pall) prior to HPLC analysis.

The results are shown in Table 3.

TABLE 3

Expression and 2 hr Fructose to Allulose Conversion Profile of Epimerase Variants

| Variant ID | Expression [ng/mL] | Fructose_50% wt/wt, Time Point 2.0 hr, pH 5.0 | Allulose_50% wt/wt, Time Point 2.0 hr, pH 5.0 |
|---|---|---|---|
| 230338 | 16.1 | 44.07 | 0.96 |
| 256407 | 23.8 | 44.37 | 1.12 |
| 257999 | 11.8 | 44.57 | 1.25 |
| 261731 | 10.8 | 43.33 | 1 |
| 261732 | 17.6 | 43.33 | 1.59 |
| 261733 | 16.1 | 43.15 | 1.4 |
| 261734 | 15.2 | 43.22 | 1.42 |
| 261735 | 11.4 | 43.57 | 0.96 |
| 261736 | 17.4 | 43.08 | 1.33 |
| 261737 | 11.6 | 43.21 | 1.06 |
| 261738 | 21 | 43.95 | 1.51 |
| 261739 | 7.5 | 43.31 | 0.73 |
| 261740 | 15.3 | 43.48 | 1.32 |
| 261741 | 11.5 | 43.37 | 1.22 |
| 261742 | 13 | 43.52 | 1.21 |
| 261743 | 21 | 41.76 | 1.92 |
| 261744 | 13.5 | 43.19 | 1.11 |
| 261745 | 19 | 41.67 | 1.55 |
| 261746 | 24.6 | 42.05 | 1.85 |
| 261747 | 9.52 | 44.12 | 0.96 |
| 261748 | 18.3 | 43.06 | 1.37 |
| 261749 | 8.28 | 43.54 | 0.92 |
| 261750 | 16.7 | 43.88 | 1.4 |
| 261751 | 17.6 | 43.88 | 1.46 |
| 261752 | 21.4 | 42.66 | 1.82 |
| 261753 | 20.4 | 39.04 | 1.6 |
| 261754 | 19.6 | 42.83 | 1.68 |

Figure 2:
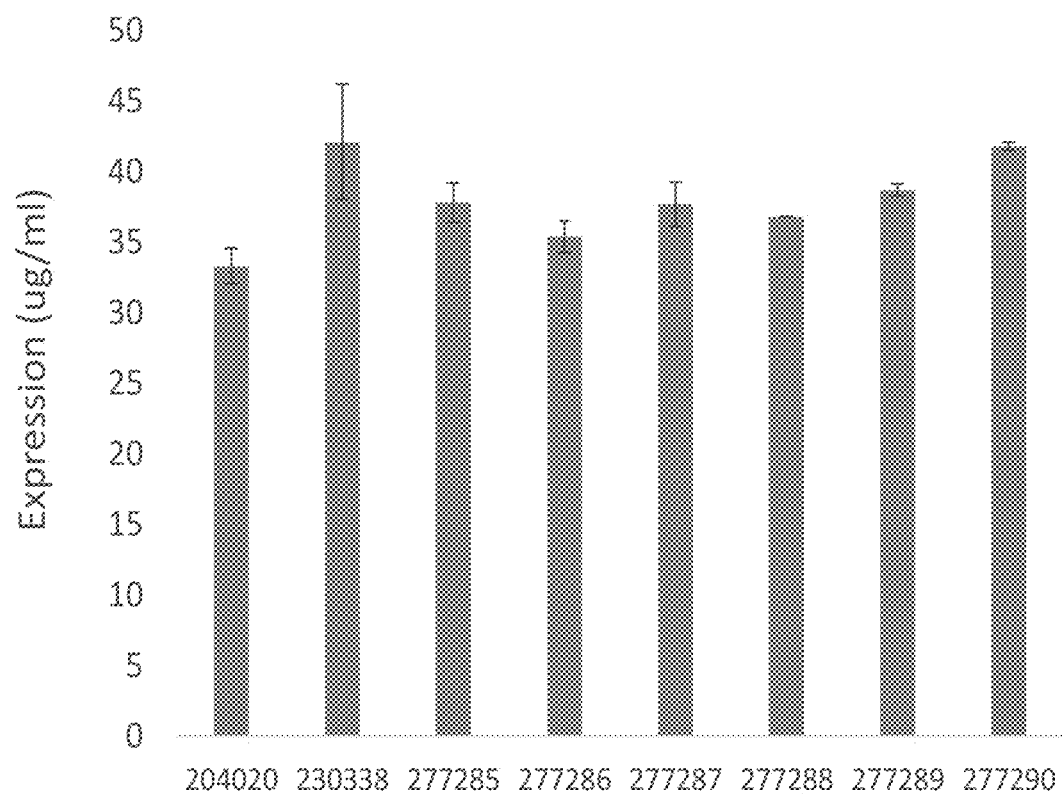
FIG. 2. Graph showing expression of wild-type epimerase (204020, SEQ ID NO:6) and of epimerase variants 230338 (SEQ ID NO:16), 277285 (SEQ ID NO:90), 277286 (SEQ ID NO:92), 277287 (SEQ ID NO:94), 277288 (SEQ ID NO:96), 277289 (SEQ ID NO:98), and 277290 (SEQ ID NO:100).
Figure 3:
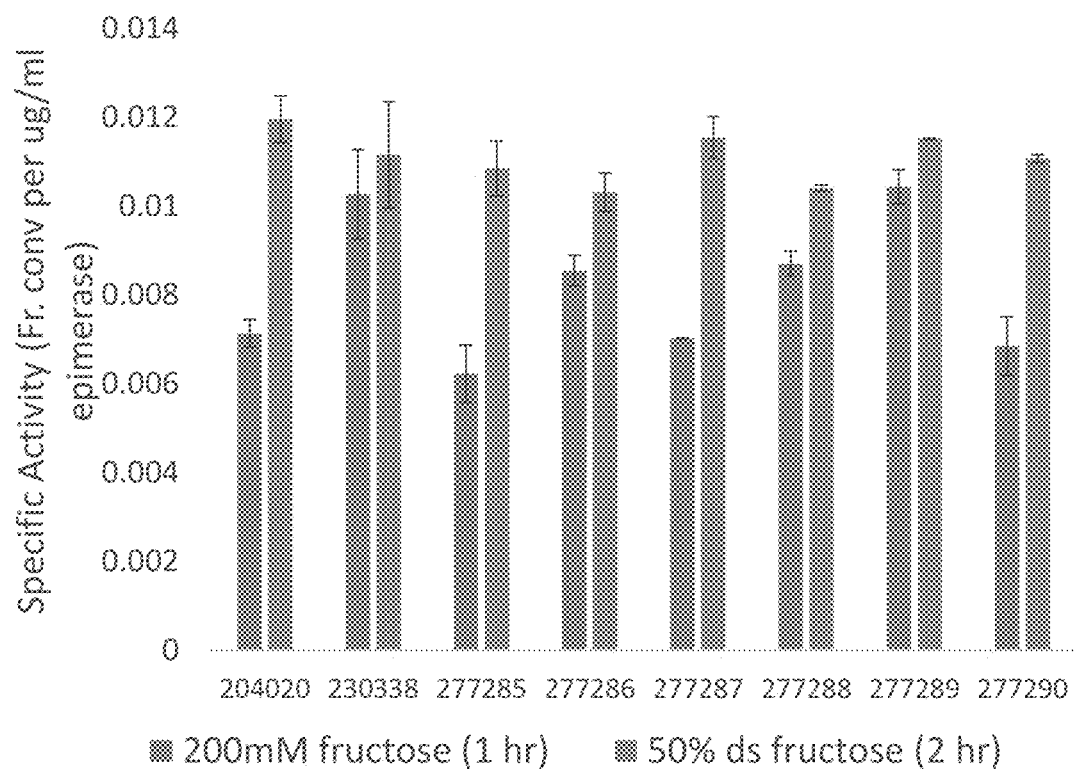
FIG. 3. Graph showing specific activities of wild-type epimerase (204020, SEQ ID NO:6) and of epimerase variants 230338 (SEQ ID NO:16), 277285 (SEQ ID NO:90), 277286 (SEQ ID NO:92), 277287 (SEQ ID NO:94), 277288 (SEQ ID NO:96), 277289 (SEQ ID NO:98), and 277290 (SEQ ID NO:100). Left bar of each pair, 200 mM; right bar of each pair, 50% DS.

Example 6. Comparative Analysis of Wild-Type Epimerase and Epimerase Variants Having One, Two, or Three Amino Acid Substitutions The fraction of fructose converted to allulose by epimerase variants having one, two, or three of the amino acid substitutions in variant 230338 (D89K, S154T, and C167I) was tested under two conditions (10% v/v clarified lysate, low (200 mM) or high (50% wt/wt) fructose, 50 mM MES, pH 5.0, and 5 mM $MgCl_2$) and compared with the wild-type epimerase. The results are shown in FIG. 1, in which the left bar of each pair of bars represents the fraction of conversion of fructose to allulose after 1 hour, starting with 200 mM fructose, and the right bar of each pair of bars represents the fraction of conversion of fructose to allulose after 2 hours, starting with 50% wt/wt fructose. The amino acid substitutions present in each variant are shown in the grid above the bar graph, and the amino acid sequences of the variants are provided in SEQ ID NO:16 (variant 230338), SEQ ID NO:90 (variant 277285), SEQ ID NO: 92 (variant 277286), SEQ ID NO: 94 (variant 277287), SEQ ID NO: 96 (variant 277288), SEQ ID NO: 98 (variant 27289), and SEQ ID NO:100 (variant 27290). "204020" is the wild-type epimerase (SEQ ID NO:6). Epimerase expression (µg/ml) is shown in FIG. 2. Specific activity (fructose converted per µg/ml of epimerase) is shown in FIG. 3.

This example demonstrates that the triple variant was catalytically most active under the conditions the enzyme was evaluated. The variant having all three substitutions (D89K, S154T, and C167I) had the highest expression and was most active enzyme in both 200 mM fructose and at 50% (w/w) fructose.

REFERENCES

Baba et al., "Construction of *Escherichia coli* K-12 in-frame, single-gene knockout mutants: the Keio collection," Molecular Systems Biology (2006) doi:10/1038/msb4100050, 11 pages Chu et al., "Expression, purification and activity of D-tagatose 3-epimerase from *Clostridium bolteae*," Shipin Gongye Keji 33, 198-201, 2012

Izumori et al., "Ketose 3-epimerase produced by *Arthrobacter globiformis*, method for converting ketose using the epimerase, and method for manufacture of ketose using the epimerase," WO 2014109254.

Kim et al., "Characterization of an *Agrobacterium tumefaciens* D-psicose 3-epimerase that converts D-fructose to D-psicose," Applied and Environmental Microbiology 72, 981-85, 2006

Li et al., "Overexpression of -psicose 3-epimerase from *Clostridium cellulolyticum* H10 in *Bacillus subtilis* and its prospect for -psicose production," Advance Journal of Food Science and Technology 5, 264-69, 2013

Mu et al., "A strategy for bioproduction of rare sugars: Izumoring," Zhongguo Shengwu Gongcheng Zazhi 27, 129-36, 2007

Mu et al., "Recent advances on applications and biotechnological production of D-psicose," Applied Microbiology and Biotechnology 94, 1461-67, 2012

Phan et al., "Development of a strong intracellular expression system for *Bacillus subtilis* by optimizing promoter elements," J Biotechnol. 157, 167-72, 2012

Wagner et al., "Practical Aspects of Integrated Operation of Biotransformation and SMB Separation for Fine Chemical Synthesis," Organic Process Research & Development 16, 323-30, 2012

Woodyer & Armentrout, "Recombinant ketose 3-epimerases for conversion of fructose to psicose," WO 2014049373

Zhang et al., "Characterization of a Metal-Dependent D-Psicose 3-Epimerase from a Novel Strain, *Desmospora* sp. 8437, J. Agricultural and Food Chemistry 61, 11468-76, 2013 Zhang et al., "Characterization of D-tagatose-3-epimerase from *Rhodobacter sphaeroides* that converts d-fructose into D-psicose," Biotechnology Letters 31, 857-62, 2009

Zhou et al, "Immobilization of D-tagatose 3-epimerase," Shipin Gongye Keji 33, 197-200, 2012

The invention claimed is:

1. A nucleic acid encoding a protein, wherein the amino acid sequence of the protein is a variant of SEQ ID NO: 6 selected from the group consisting of SEQ ID NOS:16, 18, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, and 100 wherein said variant protein exhibits higher catalytic activity in converting fructose to allulose than the protein according to SEQ ID NO:6.

2. A microorganism comprising the nucleic acid of claim 1.

3. The microorganism of claim 2, wherein the microorganism is selected from the group consisting of *Bacillus licheniformis, Saccharomyces cerevisiae, Schizosaccharomyces pombe, Pseudomonas putida, Pichia* sp., *Aspergillus* sp., *Trichoderma reesei, Corynebacterium glutamicum, E. coli,* and *B. subtilis*.

4. The protein encoded by the nucleic acid sequence according to claim 1.

5. A solid matrix comprising the protein of claim 4.

6. A column comprising the solid matrix of claim 5 and configured to receive an input solution comprising fructose over the solid matrix and to permit exit of an output solution comprising allulose.

7. A method of producing a protein comprising an amino acid sequence selected from the group consisting of SEQ ID NOS:16, 18, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, and 100, comprising:
(a) culturing the microorganism of claim 2; and
(b) recovering the protein.

8. A method of producing allulose, comprising contacting a solution comprising fructose with a protein of claim 4 for a time and under conditions suitable to convert at least a portion of the fructose to allulose.

* * * * *